United States Patent [19]

Lee

[11] Patent Number: 5,273,991
[45] Date of Patent: Dec. 28, 1993

[54] IMIDAZOLE-CONTAINING COMPOSITIONS AND METHODS OF USE THEREOF ANALOGS OF DISTAMYCIN

[75] Inventor: Moses N. F. Lee, Greenville, S.C.

[73] Assignee: Research Corporation Technologies, Inc., Tucson, Ariz.

[21] Appl. No.: 21,888

[22] Filed: Jul. 29, 1992

[51] Int. Cl.$^5$ .................. A61K 31/415; C07D 403/02; C07D 403/10; C07D 403/14
[52] U.S. Cl. ...................... 514/397; 514/398; 514/400; 548/315.7; 548/328.1; 548/328.5; 548/311.1; 548/315.1
[58] Field of Search .................. 548/336, 312.7, 328.1, 548/328.5, 311.1, 351; 514/397, 398, 400

[56] References Cited

U.S. PATENT DOCUMENTS 4,738,980  4/1988  Arcamone et al. ................. 514/422
4,912,199  3/1990  Lown et al. .......................... 530/331

OTHER PUBLICATIONS

Arcamone et al. II (1989) "Synthesis, DNA-Binding Properties, and Antitumor Activity of Novel Distamycin Derivatives", *J. Med. Chem.* 32, 774–778.
Burckhardt et al. (1989) "Variation of DNA Sequence Specificity of DNA-Oligopeptide Binding Ligands Related to Netropsin: Imidazole-Containing Lexitropsins", *Biochimica et Biophysica Acta* 11–18.
Hartley et al. (1988) "DNA Sequence Specificity of Antitumor Agents", *Acta Oncologica* 27, 503–510.
Kissinger et al. (1987) "Molecular Recognition Between Oligopeptides and Nucleic Acids. Monocationic Imidazole Lexitropsins that Display Enhanced GC Sequence Dependent DNA Binding", *biochemistry* 26, 5590–5595.
Krowicki et al. (1987) "Synthesis of Novel Imidazole-Containing DNA Minor Groove Binding Oligopeptides Related to the Antiviral Antibiotic Netropsin", *J. Org. Chem.* 52, 3493–3501.
Kumar et al. (1990) "Sequence Specific Molecular Recognition and Binding by a GC Recognizing Hoechst 33258 Analogue to the Decadeoxyribonucleotide d--CATGGCCATG: Structural and Dynamic Aspects Deduced from High Field $^1$H-NMR Studies", *Journal of Biomolecular Structure & Dynamics* 8, 331–357.
Lee et al. I (1988) "Structural and Dynamic Aspects of Binding of a Prototype Lexitropsin to the Decadeoxyribonucleotide d(CGCAATTGCG)$_2$ Deduced from High-Resolution $^1$H NMR Studies", *Biochemistry* 27, 445–455.
Lee et al. II (1988) "Sequence Specific Molecular Recognition and Binding of a Monocationic Bis-Imidazole Lexitropsin to the Decadeoxyribonucleotide d[GATCCGTATG]. (CATACGGATC)]: Structural and Dynamic Aspects of Intermolecular Exchange Studied by $^1$H NMR", *Journal of Biomolecular Structure & Dynamics* 5, 1059–1087.

(List continued on next page.)

Primary Examiner—Floyd D. Higel
Attorney, Agent, or Firm—Scully, Scott, Murphy & Presser

[57] ABSTRACT

The present invention relates to oligopeptide derivatives that are conjugated to DNA alkylating agents, having the formula

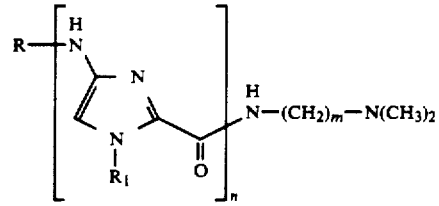

wherein m is 0 to 4; n is 2 to 4; each $R_1$ is the same or different and is hydrogen or $C_1$–$C_4$ alkyl; and R is a DNA alkylating moiety. The present invention is further directed to pharmaceutical compositions thereof, and method for treatment of cancer using the subject compounds.

44 Claims, No Drawings

OTHER PUBLICATIONS

Lee et al. III (1988) "Molecular Recognition Between Oligopeptides and Nucleic Acids: Influence of van der Waals Contacts in Determining the 3'-Terminus of DNA Sequences Read by Monocationic Lexitropsins", *J. Am. Chem. Soc.* 110, 3641-3649.

Lee et al. IV: (1989) "Molecular Recognition Between Oligopeptides and Nucleic Acids. Specificity of Binding of a Monocationic Bis-Furan Lexitropsin to DNA Deduced from Footprinting and $^1$H NMR Studies", *Journal of Molecular Recognition* 2, 84-93.

Lee et al. V (1988) "Structural and Dynamic Aspects of the Sequence Specific Binding of Netropsin and its Bis-Imidazole Analogue on the Decadeoxyribonucleic d-[CGCAATTGCG]$_2$", *Journal of Biomolecular Structure & Dynamics* 5, 939-949.

Lown (1988) "Lexitropsins: Rational Design of DNA Sequence Reading Agents as Novel Anti-Cancer Agents and Potential Cellular Probes", *Anti-Cancer Drug Design* 3, 25-40.

Lown et al. II (1986) "Structure-Activity Relationship of Novel Oligopeptide Antiviral and Antitumor Agents Related to Netropsin and Distamycin", *J. Med. Chem.* 29, 1210-1214.

Lown et al. III (1989) "Novel Linked Antiviral and Antitumor Agents Related to Netropsin and Distamycin: Synthesis and Biological Evaluation", *J. Med. Chem.* 32, 2368-2375.

Lown et al. IV (1986) "Molecular Recognition Between Oligopeptides and Nucleic Acids: Novel Imidazole-Containing Oligopeptides Related to Netropsin that Exhibit Altered DNA Sequence Specificity", *Biochemistry* 25, 7408-7416.

Mazurek et al. (1991) "The Binding of Prototype Lexitropsins to the Minor Groove of DNA: Quantum Chemical Studies", *Journal of Biomolecular Structure & Dynamics* 9, 299-313.

Calabresi et al. "Antiproliferative Agents and Drugs Used for Immunosuppression", *Goodman and Gilman's The Pharmacological Basis of Therapeutics* 6th Edition, Chapter 55, 1256-1272 (1978).

Monks et al. (1991) "Feasibility of a High-Flux Anticancer Drug Screen Using a Diverse Panel of Cultured Human Tumor Cell Lines", *Journal of the National Cancer Institute* 82, 757-766.

IMIDAZOLE-CONTAINING COMPOSITIONS AND METHODS OF USE THEREOF ANALOGS OF DISTAMYCIN

FIELD OF THE INVENTION

The present invention is directed to oligopeptide derivatives and pharmaceutical compositions containing said oligopeptide derivatives. The oligopeptide derivatives of the present invention are useful as anticancer agents.

BACKGROUND OF THE INVENTION

The family of naturally occurring oligopeptide antibiotics includes amidomycin, anthelvencins A and B, distamycin, kikumycins A and B, netropsin and norformycin. The best characterized members of this family, distamycin and netropsin, exhibit antibiotic, antiviral and antitumor activity. However, the clinical use of these agents has been limited by their high cytotoxicity.

Netropsin and distamycin interact with DNA in a sequence-specific and groove-selective manner by binding to specific nucleotide sequences [$(AT)_4$ and $(AT)_5$, respectively] within the minor groove of B-DNA (Hahn [1975] in *Antibiotics III. Mechanism of Action of Antimicrobial and Antitumor Agents*, Corcoran and Hahn, eds., Springer Verlag, New York, 79). The firm and sequence specific binding of netropsin is the net result of specific hydrogen bonding, electrostatic attraction and van der Waals interactions (Kopka et al. [1985]*Proc. Natl. Acad. Sci. U.S.A.* 82, 1376 "Kopka et al.").

Lown et al. (1986) *Biochemistry* 25, 7408, report the characterization of derivatives of netropsin in which each of the pyrrole units is successively replaced by an imidazole moiety, as well as di- and triimidazole-containing derivatives. The synthesis of the compounds is reported in Krowicki et al. (1987) *J. Org. Chem.* 52, 3493. DNA binding studies revealed a gradual change in base preference upon replacing pyrrole by imidazole, indicating that the molecular recognition process is complex. In a related study, high field $^1$H—NMR was used to compare the sequence specific binding of netropsin and the bis-imidazole analog to a the decadeoxyribonucleotide d-[CGCAATTGCG]$_2$ (Lee et al. [1988]*J. Biomol. Struct. Dyn.* 5, 939). Drug-induced chemical shift changes suggest that the bisimidazole moiety of the analog can accept GC sites, although it binds primarily at AATT. In an analogous study with a netropsin derivative in which one pyrrole moiety was substituted by imidazole, the drug appeared to bind at the AATT site in the minor groove of the DNA (Lee et al. (1988) *Biochemistry* 27, 445). Quantum chemical studies indicate that the monosubstituted derivative is capable of binding to $(GC)_n$ sequences, but the binding energy for $(GC)_n$ is reduced relative to $(AT)_n$ by approximately one half. Furthermore, a comprehensive circular dichroism study (Burckhardt et al. [1989]*Biochim. Biophys. Acta* 1009, 11) demonstrates that while imidazole substituted netropsin analogs show decreased binding preference for AT pairs, a real specificity for GC sequences is not observed. Lown et al. (1986) *J. Med. Chem.* 29, 1210, report that the mono- and di-imidazole substituted netropsin analogs lack cytostatic activity against various tumor cell lines, and the analog with three imidazole moieties has moderate cytostatic activity which is less than that of distamycin. Antiviral activity of the analogs is specific for vaccinia virus and is less than that of the parent compounds.

Kissinger et al. (1987) *Biochemistry* 26, 5590 disclose the synthesis of a series of netropsin derivatives in which the guanidinium group of the amino terminus of netropsin is replaced with an N-formyl group, and none, one or both of the N-methylpyrrole groups are replaced by N-methylimidazole. The replacement of the guanidinium group with a formyl group renders the compounds monocationic rather than dicationic. DNAase 1 footprinting studies suggest that the bis(imidazole) analog binds to the sequence 5'-CCGT-3' or 5'-ACGG-3'. The contribution of the substitution of the guanidinium group with a formyl group is not clear, since the monocationic analog possessing two N-methylpyrrole groups exhibited binding that was very similar to the binding of netrosin. The biological activity of the analogs was not assessed. The specific binding of the monocationic bis(imidazole) analog to the base sequence 5'-CCGT3' was confirmed by $^1$H—NMR studies (Lee et al. [1988]*J. Biomol. Struct. Dyn.* 5, 1059).

Less et al. (1988) *J. Amer. Chem. Soc.* 110, 3641, disclose the synthesis of monocationic netrospin analogs with one or two methylene groups at the C-terminus. The analog with one methylene group exhibited preferential binding for the sequence ATTG on the decadeosyribonucleotide [CGCAATTGCG]$_2$, while the analog with two methylene groups exhibited a preference for the sequence AATT, as determined by chemical shift changes.

Lown et al. (1989) *J. Med. Chem.* 32, 2368 and U.S. Pat. No. 4,912,199 to Lown et al. discloses oligopeptides structurally related to distamycin and netrospin in which the heterocyclic moieties are linked by polymethylene bridges or dicarboxylic acid derivatives, respectively. Enhanced antitumor activity against certain cell types and antiviral activity specific for vaccinia virus as a result of introduction of polymethylene linkers ($[CH_2]_n$ with n=1,2 and 6-8) was attributed to increased lipophilicity promoting cellular uptake, since DNA binding is comparable to that of the parent compounds.

U.S. Pat. No. 4,738,980 to Arcamone et al. ("Arcamone et al. I") and Arcamone et al. (1989) *J. Med. Chem.* 32, 774 ("Arcamone et al. II") disclose pyrrole-containing oligopeptide derivatives containing an alkylating group at the N-terminus. In Arcamone et al. II, derivatives containing an N,N-bis(2-chloroethyl) group displayed in vitro cytotoxicity against certain tumor cell lines and in vivo antitumor activity against murine L1210 leukemia The present invention provides imidazole-substituted oligopeptide derivatives that are conjugated to DNA alkylating agents. The compounds of the present invention are useful as antitumor agents.

SUMMARY OF THE INVENTION

The present invention is directed to oligopeptide derivatives that are conjugated to DNA alkylating agents. The compounds of the present invention are represented by the formula I:

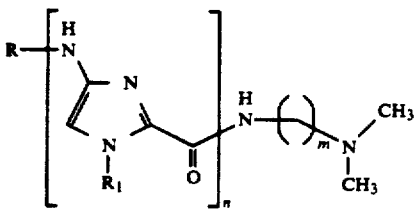

wherein
m is 0 to 4;
n is 2 to 4;
each $R_1$ is the same or different and is hydrogen or $C_1$-$C_4$ alkyl; and R is a DNA alkylating moiety. In a preferred embodiment,
R is
—$CO(CH_2)_pR_3$;
—$CO(CH_2)_pCH(R_3)_2$;
—$CO(CH_2)_pC(R_3)_3$;
—$(CH_2)_pAN(R_4)_2$; or
—$(CO)(CH_2)_pAN(R_4)_2$, wherein p is 0–4; $R_3$ is halogen; A is a divalent ortho-, meta- or para-substituted phenyl group; and $R_4$ is $C_2$-$C_4$ alkyl 2-substituted by halogen.

Another aspect of the present invention is directed to a method for the treatment of cancer by administering the compounds of the present invention to a patient for a time and under conditions sufficient to effect inhibition of cancerous growth.

Yet another aspect of the present invention provides pharmaceutical compositions containing the compounds of the invention in combination with pharmaceutically acceptable carriers.

DETAILED DESCRIPTION OF THE INVENTION

The present invention is directed to oligopeptide derivatives that are conjugated to DNA alkylating agents. The compounds of the present invention are represented by the formula:

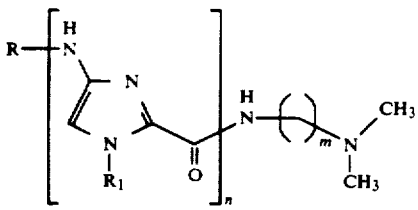

wherein
m is 0 to 4;
n is 2 to 4;
each $R_1$ is the same or different and is hydrogen or $C_1$-$C_4$ alkyl; and R is a DNA alkylating moiety. For example, R can be a derivative of a nitrogen mustard, nitrosourea, aziridine, methanesulfonate ester or epoxide. In a preferred embodiment,
R is
—$CO(CH_2)_pR_3$;
—$CO(CH_2)_pCH(R_3)_2$;
—$CO(CH_2)_pC(R_3)_3$;
—$(CH_2)_pAN(R_4)_2$; or
—$(CO)(CH_2)_pAN(R_4)_2$, wherein p is 0–4; $R_3$ is halogen; A is a divalent ortho, meta- or para-substituted phenyl group; and $R_4$ is $C_2$-$C_4$ alkyl 2 substituted by halogen.

As used herein, the terms $C_1$-$C_4$ alkyl group and $C_2$-$C_4$ alkyl group refer to alkyl groups containing one to four and two to four carbon atoms, respectively. The alkyl groups may be straight chain or branched and include such groups as methyl, ethyl, 1-propyl, 2-propyl, 1-butyl, 2-butyl. The preferred $C_1$-$C_4$ alkyl group is methyl. The preferred $C_2$-$C_4$ alkyl group is ethyl.

Preferred compounds according to Formula I are those in which m is 0 or 2, n is 2 or 3, p is 0 or 1 and $R_1$ is methyl.

When $R_3$ is a halogen, it is preferably chlorine or bromine.

When A is a divalent phenyl group, it is preferably para-substituted.

$R_4$ is preferably 2-chloroethyl.

The preferred compounds of the present invention are listed below:

N-(N',N'-dimethylamino)-1-methyl-4-{4-[4,4-bis(2-chloroethyl)aminobenzamido]-1-methylimidazole-2-carboxamido}imidazole-2-carboxamide (hereinafter referred to as Compound 5)

N-(N',N'-dimethylaminoethyl)-1-methyl-4-{4-[4,4-bis(2-chloroethyl)aminobenzamido]-1-methylimidazole-2-carboxamido}imidazole-2-carboxamide (hereinafter referred to as Compound 6)

N-(N',N'-dimethylaminoethyl)-1-methyl-4-{1-methyl-4-[4-(4,4-bis-(2-chloroethyl)aminobenzamido)-1-methylimidazole-2-carboxamido]imidazole-2-carboxamido}imidazole-2-carboxamide (hereinafter referred to as Compound 7)

N-(N',N'-dimethylaminoethyl)-1-methyl-4-{1-methyl-4-[4-(4,4-bis-(2-chloroethyl)aminobenzylamino)-1-methylimidazole-2-carboxamido]imidazole-2-carboxamido}imidazole-2-carboxamide (hereinafter referred to as Compound 8)

N-(N',N'-dimethylaminoethyl)-1-methyl-4-{4-[4,4-bis(2-chloroethyl)aminophenyl-1-butanamido]-1-methylimidazole-2-carboxamido}imidazole-2-carboxamide (hereinafter referred to as Compound 9)

N-(N',N'-dimethylaminoethyl)-1-methyl-4-{1-methyl-4-[4-(4,4-bis(2-chloroethyl)aminophenyl-1-butanamido]-1-methylimidazole-2-carboxamido]imidazole-2-carboxamido}imidazole-2-carboxamide (hereinafter referred to as Compound 10)

N-(N',N'-dimethylaminoethyl)-1-methyl-4-[4-(chloroacetamido)-1-methylimidazole-2-carboxamido)imidazole-2-carboxamide (hereinafter referred to as Compound 11)

N-(N',N'-dimethylaminoethyl)-1-methyl-4-[4-(bromoacetamido)-1-methylimidazole-2-carboxamido]imidazole-2-carboxamide (hereinafter referred to as Compound 12)

The compounds of the present invention contain two, three or four imidazole groups joined by carboxamido linkages. The compounds of the present invention contain a C-terminal dimethylamino moiety rendering the present compounds more stable and less hygroscopic than the naturally occurring oligopeptide distamycin. The N-terminus of the subject compounds contains a DNA alkylating moiety. DNA alkylating agents are well-known to one of ordinary skill in the art and include, for example, nitrogen mustards (e.g., chlorambucil, mechlorethamine hydrochloride and melphalan hydrochloride); nitrosoureas, aziridines, methanesulfonate esters and epoxides. The substitution of imidazole groups for the pyrrole groups of distamycin results in the present compounds which have increased GC sequence tolerance relative to distamycin. Accordingly, the present compounds can act as vectors for the delivery of the alkylating moiety to GC rich regions of a host genome. GC rich sequences are common in mammalian genomes and present in the flanking regions of a number of oncogenes and viral sequences, and thus are of interest as potential sites of interference with cellular function, e.g. by DNA alkylation.

The compounds of the invention can be prepared by art recognized methods A general synthetic approach is described and illustrated in Scheme 1 below.

the presence of a solvent and, preferably using an excess of the amine. Suitable solvents are chloroform ($CHCl_3$), methylene chloride ($CH_2Cl_2$), tetrahydrofuran (THF), acetonitrile ($CH_3CH$), dimethylsulfoxide (DMSO), hexamethylphosphoric triamide (HMPT), pyridine, dimethylformamide (DMF), dioxane, dimethoxyethane (DME), ether, water and low boiling alcohols such as methanol, ethanol, propanol and butanol. The preferred solvents are THF and $CH_2Cl_2$. The reaction is carried out generally at temperatures of about $-50°$ C. to $50°$ C., preferably at $-20°$ C., and for a period of 5 minutes to 50 hours, preferably 16 hours, followed by warming to room temperature.

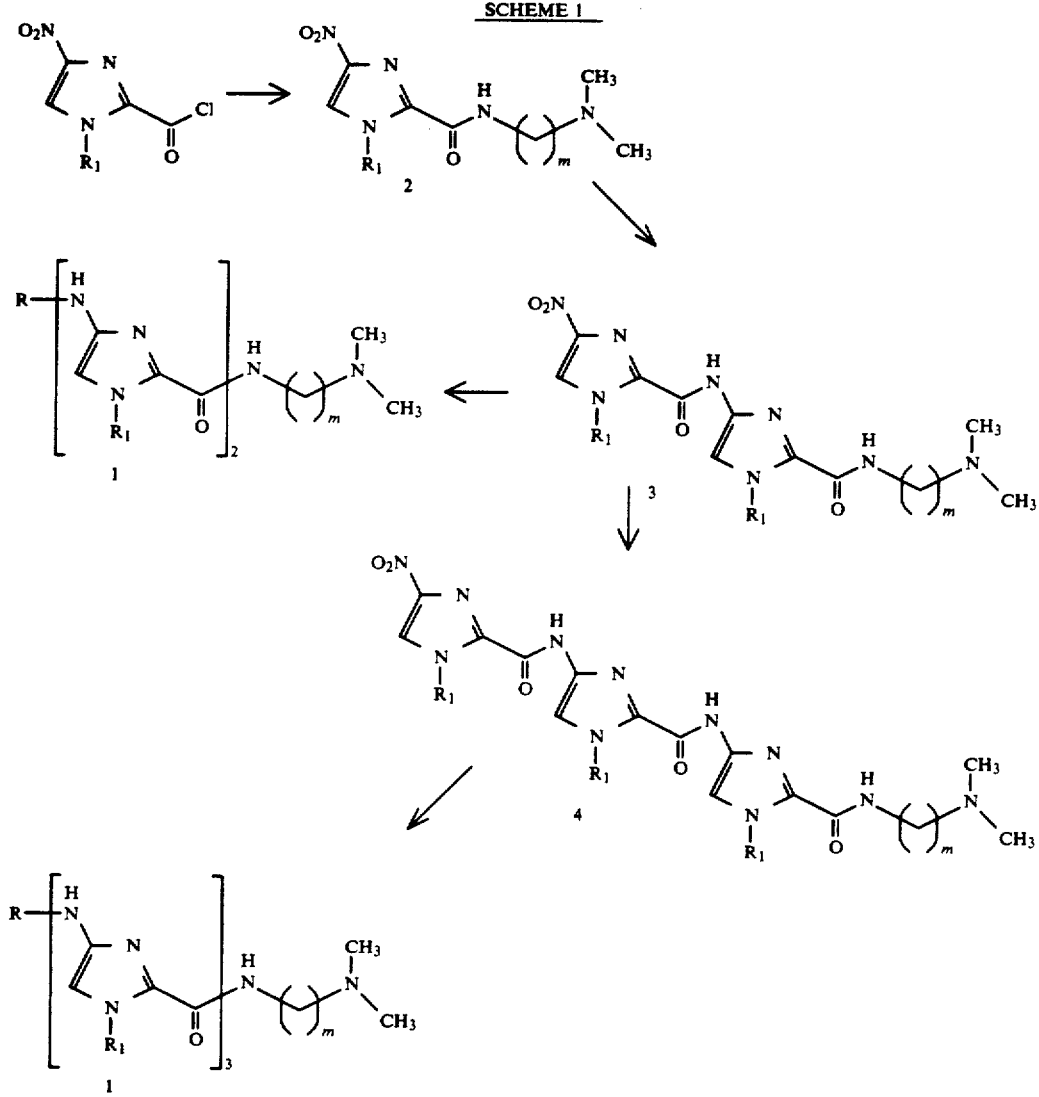

SCHEME 1

1-substituted-4-nitroimidazole-2-carboxylic acid is first converted to its acid chloride by heating a mixture of the acid, oxalyl chloride and dry tetrahydrofuran (THF) using a published procedure (Krowicki et al., 1987). Reaction of the acid chloride with an amine such as N,N-dimethylhydrazine, N,N-dimethylmethylenediamine, N,N-dimethylethylenediamine, N,N,-dimethylpropylenediamine and N,N-dimethylbutylenediamine, preferably N,N-dimethylhydrazine and N,N-dimethylethylenediamine, gives compound 2 of Scheme 1. The reaction is preferably carried out in Reduction of the nitro group of compounds 2, 3 and 4 to provide the corresponding amines can be accomplished using standard reduction methods such as catalytic hydrogenation over Pd on charcoal, $PtO_2$, Ni and others, and dissolved metal reduction such as $FeCl_2/HCl$, $SnCl_2/HCL$ and others. The preferred method is catalytic hydrogenation over Pd on charcoal and preferably is performed in the presence of a solvent. Suitable solvents are ethyl acetate, THF, acetonitrile, DMF, DMSO, dioxane and the low boiling alcohols such as methanol, ethanol, propanol and butanol. Methanol is preferred. The reaction is carried out generally at a temperature of about 0° C. to 50° C., preferably 25° C., at pressure between 1 and 3 atmospheres, preferably at atmospheric pressure, and generally for a period of 0.5 hour to 48 hours. The resulting amines such as N-(N',N'-dimethylaminoethyl)-1-methyl-4-aminoimidazole-2-carboxamide; N-(N',N'-dimethylaminoethyl)-1-methyl-4-[1-methyl-4-aminoimidazole-2-carboxamido]imidazole-2-carboxamide; N-(N',N'-dimethylaminoethyl)-1-methyl-4-[1-methyl-4-[1-methyl-4-aminoimidazole-2-carboxamido]imidazole-2-carboxamido]imidazole-2-carboxamide; N-(N',N'-dimethylamino)-1-methyl-4-aminoimidazole-2-carboxamide; N-(N',N'-dimethylamino)-1-methyl-4-[1-methyl-4-[1-methyl-4-aminoimidazole-2-carboxamido]imidazole-2-carboxamide are unstable and are used directly in the next condensation step.

The reaction of an amine derived from the reduction of compounds of the formula 2 of Scheme 1 such as N-(N',N'-dimethylaminoethyl)-1-substituted-4-aminoimidazole-2-carboxamide or N-(N',N'-dimethylamino)-1-substituted-4-aminoimidazole-2-carboxamide with 1-methyl-4-nitroimidazole-2-carbonyl chloride gives Compound 3 of Scheme 1. The reaction is preferably performed in the presence of a solvent and preferably using an excess of the acid chloride. The solvent is preferably an inert organic solvent, e.g. DMSO, DMF, THF, methylene chloride, chloroform, acetonitrile, dioxane, DME, HMPT, pyridine, among others Methylene chloride and THF are the preferred solvents. The reaction temperature may range from −50° C. to 50° C., preferably −20° C. followed by warming to room temperature, and generally requires a period of 5 minutes to 48 hours.

The reaction of the amines derived from the reduction of compounds of the formula 3 such as N-(N',N'-dimethylaminoethyl)-1-methyl-4-[1-methyl-4-aminoimidazole-2-carboxamido]imidazole-2-carboxamide, N-(N',N'-dimethylamino)-1-methyl-4-[1-methyl-4-aminoimidazole-2-carboxamido]imidazole-2-carboxamide with 1-substituted-4-nitroimidazole-2-carbonyl chloride gives Compound 4 of Scheme 1. The reaction is preferably performed in the presence of a solvent and preferably using an excess of the acid chloride. The solvent is preferably an inert organic solvent, e.g. DMSO, DMF, THF, methylene chloride, chloroform, acetonitrile, dioxane, DME, HMPT, pyridine, among others Methylene chloride and THF are the preferred solvents The reaction temperature may range from −50° C. to 50° C., preferably −20° C., followed by warming to room temperature, and generally requires a period of 5 minutes to 48 hours.

The amines such as N-(N',N'-dimethylaminoethyl)-1-methyl-4-[1-methyl-4-aminoimidazole-2-carboxamido]imidazole-2-carboxamide, N-(N',N'-dimethylamino)-1-methyl-4-[1-methyl-4-aminoimidazole-2-carboxamido]imidazole-2-carboxamide, N-(N',N'-dimethylaminoethyl)-1-methyl-4-[1-methyl-4-[1-methyl-4-aminoimidazole-2-carboxamido]imidazole-2-carboxamido]imidazole-2-carboxamide can be covalently conjugated to a derivative of a DNA alkylating agent by art recognized methods. For example, the amine can be condensed with a carboxylic acid derivative of a DNA alkylating agent. Suitable carboxylic acid derivatives are acetyl chloride, chloroacetyl chloride, dichloroacetyl chloride, trichloroacetyl chloride, bromoacetyl chloride, iodoacetyl chloride, p-N-N-bis(2-chloroethyl)aminobenzoyl chloride, p-N,N-bis(2-chloroethyl)aminophenylbutyric chloride, benzoyl chloride, among others. The reaction is preferably performed in the presence of a solvent and preferably using an excess of the carboxylic acid derivative. The solvent is preferably an inert organic solvent, e.g. DMSO, DMF, THF, methylene chloride, chloroform, acetonitrile, dioxane, DME, HMPT, pyridine or low boiling alcohols such as methanol, ethanol, propanol, and butanol or water. Methylene chloride and THF are the preferred solvents. The reaction temperature may range from −50° C. to 50° C., preferably −20° C., followed by warming to room temperature, and generally requires a period of 5 minutes to 48 hours.

The amines such as N-(N',N'-dimethylaminoethyl)-1-methyl-4-[1-methyl-4-aminoimidazole-2-carboxamido]imidazole-2-carboxamide, N-(N',N'-dimethylamino)-1-methyl-4-[1-methyl-4-aminoimidazole-2-carboxamido]imidazole-2-carboxamide, N-(N',N'-dimethylaminoethyl)-1-methyl-4-[1-methyl-4-[1-methyl-4-aminoimidazole-2-carboxamido-imidazole-2-carboxamido]imidazole-2-carboxamide can also be condensed with aldehydes or ketones in presence of reducing agents to produce compound 1 of Scheme 1. The reaction is preferably performed in the presence of a solvent and preferably using an excess of the carbonyl reagent. Suitable aldehydes are low alkyl aldehydes such as formaldehyde, acetaldehyde, propanal, butanal and pentanal, benzaldehyde, methoxybenzaldehyde, and preferably N,N-bis(2-chloroethyl)aminobenzaldehyde. Suitable ketones are low boiling ketones such as acetone, butanone and pentanone. The reducing agent can be, for example, sodium borohydride, sodium cyanoborohydride, borane, lithium tri-t-butoxyaluminum hydride, diisopropylaluminum hydride, among others and preferably is sodium borohydride. The solvent is preferably an inert organic solvent, for example acetonitrile or a low boiling alcohol such as methanol, ethanol, propanol, and butanol, acetonitrile. The reaction temperature may range from −50° C. to 50° C., preferably 26° C., and it generally requires from about 15 minutes to 100 hours.

All possible isomers of the compound of Formula 1, both separately and in mixture, are contemplated in accordance with the present invention. Well-known procedures such as, for example, fractional crystallization or chromatography may also be followed for separating a mixture of isomers of Formula 1 into single isomers.

The compounds of Formula 1 prepared according to the above-described procedures can be purified by conventional methods such as silica gel or alumina chromatography and/or fractional crystallization from an organic solvent such as a lower aliphatic alcohol, for example methyl, ethyl or isopropyl, or dimethylformamide.

The compounds of this invention are characterized by standard spectroscopic methods, for example infrared, UV-visible, mass spectrometry, $^1$H and $^{13}$C-NMR, and elemental analyses.

The compounds of the present invention are useful as anticancer agents. Although the biological mechanism which results in anticancer activity is not fully understood, the compounds of the subject invention are capable of binding to the minor groove of double-stranded DNA and, unlike distamycin and netropsin, can tolerate GC-containing DNA. Accordingly, the DNA alkylating moiety of the compounds of the present invention can be directed to the minor groove of GC-containing regions of double-stranded DNA. One of ordinary skill in the art can determine the DNA alkylating ability of the compounds of the present invention by art-recognized methods. The formation of an irreversible adduct of DNA and a compound of the present invention is defined herein as a measure of the DNA alkylating ability of the subject compounds. The formation of an irreversible adduct can be determined by art-recognized methods. For example, a solution containing DNA and a compound of the present invention can be exhaustively dialyzed under conditions which allow unbound drug to pass out of the dialysis bag. The percentage of the compound which has been retained in the dialysis bag is considered to be covalently bound to the DNA, and is determined by comparing the UV absorption spectrum of the compound/DNA solution before and after exhaustive dialysis.

The present invention is further directed to the pharmaceutically acceptable salts of the compounds of formula 1. The salts include those prepared by standard methods with pharmaceutically acceptable inorganic acids such as hydrochloric, hydrobromic, nitric and sulfuric acids, and pharmaceutically acceptable organic acids such as citric, tartaric, maleic, fumaric, methanesulfonic and ethanesulfonic. The preferred salt is hydrochloride.

The compounds of the present invention are useful as anticancer agents. The subject compounds exhibit cytostatic activity toward tumor cells and thus are useful to inhibit the growth of various cancers such as carcinomas, e.g. mammary carcinoma, lung carcinoma, bladder carcinoma, pancreatic carcinoma, colon carcinoma, ovarian and endometrial carcinomas. Other cancers which can be treated by the compounds of the present invention are sarcomas, e.g. soft tissue and bone sarcomas, and hematological malignancies such as leukemias.

Another aspect of the present invention is directed to a method for treatment for cancer by administering the compounds of the present invention to a patient for a time and under conditions to effect inhibition of cancerous growth.

The present compounds may be administered to a host as a pharmaceutical composition in a therapeutically effective amount. The pharmaceutical compositions contain a therapeutically effective dosage of the compounds according to the present invention together with a pharmaceutically acceptable carrier.

The compositions can be administered by well-known routes including oral, intravenous (if soluble), intramuscular, intranasal, intradermal, subcutaneous, parenteral, enteral and the like. Depending on the route of administration, the pharmaceutical composition may require protective coatings.

The pharmaceutical forms suitable for injectionable use include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyol such as glycerol, propylene glycol, polyethylene glycol, suitable mixtures thereof, surfactants or vegetable oils. Sterilization can be accomplished by an art-recognized technique, including but not limited to, addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject compounds is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the compounds are administered orally, the pharmaceutical compositions thereof containing an effective dosage of the compound may also contain an inert diluent, an assimilable edible carrier and the like, be in hard or soft shell gelatin capsules, be compressed into tablets, or may be in an elixir, suspension, syrup or the like.

The subject compounds are thus compounded for convenient and effective administration in pharmaceutically effective amounts with a suitable pharmaceutically acceptable carrier in a therapeutically effective dosage.

The dosage depends on the age, weight and conditions of the patient and on the administration route. For example, a suitable dosage for the administration to adult humans ranges from about 0.01 to about 100 mg per kilogram body weight. The preferred dosage ranges from about 0.5 to about 5.0 mg per kilogram body weight.

As used herein, a pharmaceutically acceptable carrier includes any and all solvents, dispersion media, coatings, antibacterial and antifungal agents, isotonic agents and the like. The use of such media and agents are well-known in the art.

The following examples further illustrate the invention.

EXAMPLE 1

Synthesis of N-(N',N'-dimethylamino)-1-methyl-4-{4-[4,4-bis(2-chloroethyl)aminobenzamido]-1-methylimidazole-2-carboxamido}imidazole-2-carboxamide (Compound 5)

To a solution of 1-methyl-4-nitroimidazole-2-carboxylic acid (2.0 g, 0.012 mol) in dry THF (20 mL) was slowly added oxalyl chloride (6 mL). The solution was heated to reflux for 45 minutes, and the solvent and excess oxalyl chloride were removed under reduced pressure to give 1-methyl-4-nitroimidazole-2-carbonyl chloride as a yellow powder which was coevaporated with dry $CH_2Cl_2$ (15 mL).

A solution of 1,1-dimethylhydrazine (1.06 mL, 14.0 mmol) and dry triethylamine (2.12 mL) in dry THF (20 mL) was cooled to $-20°$ C. and placed under argon. The acid chloride from above was dissolved in dry $CH_2Cl_2$ (10 mL) and added dropwise, while stirring, and the reaction mixture was allowed to warm to room temperature over 4.5 h. The solution was evaporated to dryness in-vacuo and water was added. The suspension was extracted with methylene chloride (50 mL, 4 times), and concentration of the combined organic extracts under reduced pressure gave N-(N',N'-dimethylamino)-1-methyl-4-nitroimidazole-2-carboxamide, after drying in-vacuo (80° C.), 2.34 g (94% yield), as a yellow solid. Analytical sample was prepared for analysis by recrystallization from water. mp 154° C. TLC (2.5% MeOH/$CHCl_3$) $R_f$ 0.51. $^1H$—NMR ($CDCl_3$):

δ2.69 (s, 6H, N(CH$_3$)$_2$), 4.16 (s, 3H, N—CH$_3$), 7.80 (s, 1H, imidazole), 8.00 (s, 1H, NH). IR(Nujol): υ3375, 1670 cm$^{-1}$. MS(EI) m/z (relative intensity) 213 (M$^+$, 2) 154 (6, M—NHN(CH$_3$)$_2$).

Anal. calcd. for C$_7$H$_{11}$N$_4$O$_3$: C, 39.44; H, 5.16.
Observed: C, 39.46; H, 5.13.

A suspension of N-(N',N'-dimethylamino)-1-methyl-4-nitroimidazole-2-carboxamide (2.01 g, 9.4 mmol) and 5% Pd on charcoal (0.8 g) in chilled methanol (100 mL) was purged of air and hydrogenated at room temperature and atmospheric pressure for 4 hours. The catalyst was removed by filtration and the solvent was evaporated under reduced pressure to give N-(N',N'-dimethylamino)-1-methyl-4-aminoimidazole-2-carboxamide as a glassy solid which is unstable and used directly in the next step.

The amine from above was dissolved in dry THF (20 mL) and cooled to −20° C. The stirring reaction mixture was placed under argon and a solution of 1-methyl-4-nitroimidazole-2-carbonyl chloride (2.18 g, 11.5 mmol) in dry CH$_2$Cl$_2$ (10 mL) was added dropwise. The reaction was allowed to warm to room temperature and stirred overnight then concentrated to dryness and water was added. The suspension was filtered and the solid was washed with carbon tetrachloride and water, then dried in-vacuo (80° C.) to provide N-(N',N'-dimethylamino)-1-methyl-4-[1-methyl-4-nitroimidazole-2-carboxamido]imidazole-2-carboxamide as a pale yellow crystalline solid, 2.18 g (68.8% yield). A sample for analysis was obtained by recrystallization from water: mp 239° C. (dec.). TLC (5% MeOH/CHCl$_3$) R$_f$0.66. $^1$H—NMR (CDCl$_3$); δ2.69 (s, 6H, N(CH$_3$)$_2$), 4.07 (s, 3H, N—CH$_3$), 4.21 (s, 3H, N—CH$_3$), 7.43 (s, 1H, NH). IR (nujol: υ3397 and 1678 cm$^{-1}$. MS(EI) m/z (rel. intensity) 336 (M$^+$, 100), 293 (M+1-N(CH$_3$)$_2$, 85).

Anal. calcd. for C$_{12}$H$_{15}$N$_8$O$_4$. ½H$_2$O; C, 41.90; H 4.76.
Observed: C, 41.96; H, 4.55.

A solution of N-(N',N'-dimethylamino)-1-methyl-4-[1-methyl-4-nitroimidazole-2-carboxamido]-imidazole-2-carboxamide (0.50 g, 1.49 mmol) and 5% Pd on charcoal (0.2 g) in chilled methanol (20 mL) was purged of air and hydrogenated at room temperature for 6 hours. The catalyst was removed by filtration and the methanol evaporated under reduced pressure to give N-(N',N'-dimethylamino)-1-methyl-4-[1-methyl-4-aminoimidazole-2-carboxamido]-imidazole-2-carboxamide as an unstable yellow solid.

A suspension of N-(N',N'-dimethylamino)-1-methyl-4-[1-methyl-4-aminoimidazole-2-carboxamido]-imidazole-2-carboxamide (0.2 g, 0.60 mmol) and 5% Pd on charcoal (0.15 g) in chilled methanol (15 mL) was hydrogenated for five and a half hours. The catalyst was removed by filtration and the filtrate was concentrated to a yellow solid.

A mixture of p-N,N-bis(2-chloroethyl)aminobenzoic acid (0.16 g, 0.58 mmol), thionyl chloride (3 mL) and benzene (2 mL) was heated to reflux for 75 minutes, then the solvent and excess thionyl chloride were removed under reduced pressure to give the acid chloride as a greenish solid.

A solution of the amine in dry CH$_2$Cl$_2$ (15 mL) and dry triethylamine (84 μL) was placed under argon and cooled to −20° C. and a solution of the acid chloride in dry CH$_2$Cl$_2$ (3 mL) was added dropwise. The resulting solution was allowed to warm to room temperature overnight then concentrated to dryness. The solid residue was purified by column chromatography (silica gel), using 2.5% methanol/CHCl$_3$ eluant and doubling the methanol percentage every 100 mL to give the product (9.8 mg) as an off-white powder; Yield 3.1%. mp 108°–110° C. TLC (5% MeOH/CHCl$_3$) R$_f$0.49. $^1$H—NMR (CDCl$_3$); δ2.66 (s, 6H, N(CH$_3$)$_2$), 3.65 (t, 4H, 2NCH$_2$), 3.80 (t, 4H, 2CH$_2$Cl), 4.02 (s, 3H, N—CH$_3$), m 4.06 (s, 3H, N—CH$_3$), 6.72 (d, 2H, phenyl), 7.42 (s, 1H, imidazole), 7.56 (s, 1H, imidazole), 7.81 (d, 2H, phenyl), 7.84 (s, 1H, NH), 8.48 (s, 1H, NH), 9.42 (s, 1H, NH). IR (CHCl$_3$): υ3300, 1675, 1533 cm$^{-1}$.

UV (ethanol): λmax 310 nm.
MS(FAB, TFA-NBA) for C$_{23}$H$_{30}$N$_9$O$_3$Cl$_2$, calcd.: 550.1853.
Observed: 550.1856.

EXAMPLE 2

Synthesis of N-(N',N'-dimethylaminoethyl)-1-methyl-4-{4-[4,4-bis(2-chloroethyl)aminobenzamido]-1-methylimidazole-2-carboxamido}imidazole-2-carboxamide (Compound 6)

To a suspension of 1-methyl-4-nitroimidazole-2-carboxylic acid (3.00 g, 17.5 mmol) in dry THF (30 mL) was slowly added oxalyl chloride (12 mL). The reaction mixture was heated to reflux under a drying tube for 45 minutes at which time the excess oxalyl chloride and THF were removed under reduced pressure and the acid chloride coevaporated twice with dry CH$_2$Cl$_2$ (20 mL each) yielding 1-methyl-4-nitroimidazole-2-carbonyl chloride as a yellow powder.

To a cooled (−20° C., CCl$_4$/N$_2$ bath) and stirred solution of N,N-dimethylethylenediamine (2.3 mL, 21 mmol), dry triethylamine (3.16 mL, 22.8 mmol), and dry THF (30 mL) was added a solution of the acid chloride in dry THF (30 mL). The reaction was kept at 20° C. for an additional 15 minutes and then allowed to warm to room temperature and to stir under a drying tube at room temperature (17 h). The reaction was then concentrated under reduced pressure to an off-white solid which was suspended in water (100 mL) and then filtered. The solid was dried in vacuo at 80° C. The filtrate was extracted four times with CH$_2$Cl$_2$ (70 mL). The organic layers were combined and dried (Na$_2$SO$_4$) then concentrated under reduced pressure to a yellow powder of N-(N',N'-dimethylaminoethyl)-1-methyl-4-nitroimidazole-2-carboxamide. Total yield; 3.85 g (16.0 mmol, 91%). mp 126°–128° C.; TLC (10% MeOH/CHCl$_3$) R$_f$0.29 ; $^1$H—NMR (CDCl$_3$): δ2.27 (s, 6H, N',N'-dimethyls), 2.52 (t, 2H, CH$_2$NMe$_2$), 3.48 (q, 2H, NCH$_2$C) 4.15 (s, 3H imidazole-1-methyl), 7.6 (br s, 1H, amide-NH). IR (Nujol): υ3380, 2760, 1675 1540, 1300, cm$^{-1}$; MS(EI) m/z (relative intensity) 241 (M$^+$, 6); 197 (M—(CH$_2$)$_2$N(CH$_3$)$_2$, 100);

Anal. Calcd. for C$_9$H$_{15}$N$_5$O$_3$: C, 44.94; H, 6.33.
Observed: C, 45.31; H, 6.08.

A solution of N-(N',N'-dimethylaminoethyl)-1-methyl-4-nitroimidazole-2-carboxamide (2.00 g, 8.31 mmol) in methanol (100 mL) was hydrogenated over 5% Pd on carbon (796 mg) at room temperature and atmospheric pressure until TLC analysis indicated complete reduction of the starting material (2.5 h). The catalyst was removed by filtration. The filtrate was concentrated, and the residue was coevaporated with dry CH$_2$Cl$_2$ (20 mL, twice) to give N-(N',N'-dimethylaminoethyl)-1-methyl-4-aminoimidazole-2-carboxamide as a yellow oil, which was unstable and thus used directly in the next step.

To a cooled (−20° C., CCl$_4$/liq N$_2$ bath) and stirred solution of the reduction product from above and dry triethylamine (1.5 mL, 10.8 mmol) in dry CH$_2$Cl$_2$ (40 mL) was added 1-methyl-4-nitroimidazole-2-carbonyl chloride. After the addition of the acid chloride, the reaction was kept at −20° C. for an additional 15 minutes and then allowed to warm to room temperature and to stir at room temperature overnight (17 h). After TLC analysis indicated that all of the starting material had disappeared, the reaction mixture was concentrated under reduced pressure to an orange solid. The solid was suspended in 150 mL water and filtered. The solid product was dried in vacuo at 80° C. The filtrate was extracted with $CH_2Cl_2$ (75 mL, three times). The organic layers were combined, dried ($Na_2SO_4$), and concentrated to an orange powder of N-(N',N'-dimethylaminoethyl)-1-methyl-4-[1-methyl-4-nitroimidazole-2-carboxamido]imidazole-2-carboxamide, which was dried in vacuo at room temperature. Yield: 2.09 g (5.74 mmol, 69%). mp 238°–240° C. TLC (10% MeOH/$CHCl_3$) $R_f$ 0.36. $^1$H NMR ($CDCl_3$); $^1$H NMR ($CDCl_3$): δ2.33 (s, 6H, N',N'-dimethyls), 2.55 (T, 2H, $CH_2NME_2$), 3.48 (q, 2H, $NCH_2C$), 4.05 (s, 3H, imidazole-1-methyl), 4.21 (s, 3H, imidazole-1-methyl), 7.85 (s, 1H, imidazole), 9.50 (br s, 1H, NH). IR (Nujol): 3450, 3140, 3120, 2880, 1675, 1650, 1550, 1535, 1350, 1300 cm$^{-1}$; MS(EI) m/z (relative intensity): 364 (M+, 5) 334 (M—$CH_3$)$_2$, 2).

Anal. Calcd. for $C_{14}H_{20}N_8O_4$ (364.42): C, 46.13; H, 5.54.

Observed: C, 45.95; H, 5.15.

A solution of N-(N',N'-dimethylaminoethyl)-1-methyl-4-[1-methyl-4-nitroimidazole-2-carboxamido]imidazole-2-carboxamide (501 mg, 1.38 mmol) in methanol (75 mL) was hydrogenated over 5% Pd on carbon (282 mg) at room temperature and atmospheric pressure until TLC analysis indicated complete reduction of the starting material (2.75 h). The catalyst was removed by filtration. The filtrate was concentrated, and the residue was coevaporated with dry THF (30 mL, twice) to give N-(N',N'-dimethylaminoethyl)-1-methyl-4-[1-methyl-4-aminoimidazole-2-carboxamido]imidazole-2-carboxamide as an off-white foamy solid which is unstable and was used directly in the next step.

p-N,N-Bis(2-chloroethyl)aminobenzoyl chloride was prepared by dissolving p-N,N-bis(2-chloroethyl)aminobenzoic acid (360.1 mg, 1.37 mmol) in benzene (3 mL) and thionyl chloride (3 mL) and heating to reflux under a drying tube for 1.25 h. The excess thionyl chloride and solvent were then removed under reduced pressure and the residue coevaporated with dry $CH_2Cl_2$ (10 mL, twice). To a stirred solution of N-(N',N'-dimethylaminoethyl)-1-methyl-4-[1-methyl-4-aminoimidazole-2-carboxamido]imidazole-2-carboxamide (457 mg, 1.37 mmol) in dry $CH_2Cl_2$ (40 mL) with dry triethylamine (210 μL, 1.51 mmol) was cooled to −20° C. ($CCl_4$/liq $N_2$ bath) and the above acid chloride dissolved in dry $CH_2Cl_2$ (10 mL) was added dropwise under an atmosphere of argon. The reaction mixture was kept at 20° C. for an additional 15 minutes and then allowed to stir at room temperature (22.5 h). After TLC analysis indicated that all of the starting material was gone, the reaction was concentrated under reduced pressure to an orange foam. The residue was then dissolved in $CH_2Cl_2$ (100 mL) and washed with saturated $NaHCO_3$ (100 mL) and water (100 mL) sequentially. TLC analysis of the organic layers indicated impurities so the product was purified by column chromatography (silica gel) with methanol (1%) in chloroform as eluant. The resulting pure product was precipitated from $CH_2Cl_2$ with ether and hexane and the off-white powder dried in vacuo at room temperature. Yield: 216 mg (0.37 mmol, 27%). mp (dec.) 165° C. TLC (10% MeOH/$CHCl_3$)$R_f$ 0.40. $^1$H NMR ($CDCl_3$) δ2.27 (s, 6H, N',N'-dimethyls), 2.53 (t, 2H, $CH_2NMe_2$), 3.50 (q, 2H, $NCH_2C$), 3.68 (m, 4H, chloroethyl-$CH_2$—), 3.82 (m, 4H, chloroethyl-$CH_2$—), 4.02 (s, 3H, imidazole-1-methyl), 4.06 (s, 3H, imidazole-1-methyl), 6.75 (d, 2H, phenyl), 7.39 (s, 1H, imidazole), 7.58 (s, 1H, imidazole), 7.83 (t, 1H, NH), 7.94 (d, 2H, phenyl), 8.71 (br s, 1H, NH), 9.31 (br s, 1H, NH). $^{13}$C—NMR ($CDCl_3$): δ35.6, 36.7, 40.2, 45.2, 53.3, 57.9, 111.2, 113.3, 114.6, 122.0, 129.4, 133.5, 135.4, 136.9, 149.0, 158.8, 159.5, 163.9. IR(Nujol): υ3420, 1654, 1606, 1518, 1185, 668 cm$^{-1}$. UV ($H_2O$ ): λmax $^{216}$ (ε34051 cm$^{-1}$M$^{-1}$), 316 nm (ε22570 cm$^{-1}$M$^{-1}$). MS (FAB, TFA-NBA) m/z (relative intensity): 578 (M+, 80). Anal. calcd. for $C_{25}H_{33}Cl_2N_9O_3$. ½$H_2O$: C, 51.10; H, 5.84. Observed C, 51.11; H, 5.72.

EXAMPLE 3

Synthesis N-(N',N'-dimethylaminoethyl)-1-methyl-4-{1-methyl- [-4-[4-(4,4-bis-(2-chloroethyl)aminobenzamido)-1-methylimidazole-2-carboxamido]imidazole-2-carboxamido}imidazole-2-carboxamide (Compound 7)

To a solution of N-(N',N'-dimethylaminoethyl)-1-methyl-4-[1-methyl-4-aminoimidazole-2-carboxamido]imidazole-2-carboxamide (3.0 g, 8.5 mmol) in dry $CH_2Cl_2$ (50 mL) was added a solution of 1-methyl-4-nitroimidazole-2-carbonyl chloride (1.4 g, 8.5 mmole) in dry THF (25 mL) in a dropwise fashion. The reaction mixture was kept at −20° C. for an additional 15 minutes and then allowed to stir overnight at room temperature (12.5 h). After TLC analysis indicated that all of the starting material was gone, the reaction mixture was concentrated under reduced pressure to an orange solid which was suspended in water and filtered followed by drying in vacuo at 80° C. The filtrate was extracted with $CH_2Cl_2$ (180 mL, 3×) and the combined organic layers were dried ($Na_2SO_4$), and concentrated to an orange foam, which was purified by column chromatography (silica gel) using methanol (2%) in chloroform as eluant. The pure product, N-(N',N'-dimethylaminoethyl)-1-methyl-4-{1-methyl-4-[1-methyl-4-nitroimidazole-2-carboxamido]imidazole-2-carboxamido}imidazole-2-carboxamide, was dried in vacuo at 80° C. yielding a yellow powder. Total yield 2.69 g (5.5 mmol, 65%). mp 138°–142° C. TLC (10% MeOH/$CHCl_3$)$R_f$ 0.27. $^1$H NMR ($CDCl_3$): δ2.30 (s, 6H, N',N'-dimethyls), 2.51 (t, 2H, $CH_2NMe_2$), 3.47 (q, 2H, $NCH_2C$), 4.05 (s, 3H, imidazole-1-methyl), 4.09 (s, 3H, imidazole 1-methyl), 4.21 (s, 3H, imidazole-1-methyl), 7.40 (s, 1H, imidazole), 7.48 (s, 1H, imidazole), 7.65 (t, 1H, NH), 7.87 (s, 1H, imidazole), 9.30 (s, 1H, NH), 9.55 (br s, 1H, NH). IR(Nujol): υ3380, 1658, 1536, 1303 cm$^{-1}$. MS(FAB, TFA-NBA) m/z (relative intensity): 488 (M+H+, 63), 472 (M—$CH_3$, 5).

Anal. calcd. for $C_{19}H_{25}N_{11}O_5$.½$H_2O$: C, 45.95; H, 5.24.

Observed: C, 45.88; H, 5.06.

A solution of N-(N',N'-dimethylaminoethyl) 1-methyl-4-{1-methyl-4[1-methyl-4-nitroimidazole-2-carboxamido]imidazole-2-carboxamido}imidazole-2-carboxamide (248 mg, 0.510 mmol) in methanol (35 mL) was hydrogenated over 5% Pd on carbon (118 mg) at room temperature and atmospheric pressure until TLC analysis indicated complete reduction of the starting material (5 h). The catalyst was removed by filtration. Concentration of the filtrate gave a residue which was coevaporated with dry THF (20 mL, twice) to give N-(N',N'-dimethylaminoethyl)-2-methyl-4-{1-methyl-4[1-methyl-4-aminoimidazole-2-carboxamido]imidazole-2-carboxamido}imidazole-2-carboxamide as an off-white powder. p-N,N-Bis(2-chloroethyl)aminobenzoyl chloride was prepared by dissolving p-N,N-Bis(2-chloroethyl)aminobenzoic acid (13.4 mg, 0.510 mmol) in benzene (2 mL) and thionyl chloride (2 mL) and heating to reflux under a drying tube for 1.25 h. (The solution turned from purple to green upon addition of thionyl chloride). The excess thionyl chloride and solvent were then removed under reduced pressure and the residue coevaporated with dry $CH_2Cl_2$ (10 mL, once).

The amine from above was dissolved in dry $CH_2Cl_2$ (20 ml) with dry triethylamine (71 μL, 0.51 mmol) and cooled to $-20°$ C. ($CCl_4$/liq $N_2$ bath). The acid chloride dissolved in dry $CH_2Cl_2$ (7 mL) was added dropwise to the cooled solution under argon. The reaction mixture was kept at $-20°$ C. for an additional 15 minutes and then allowed to stir at room temperature overnight (17 h). After TLC analysis indicated that all of the starting material was gone, the reaction was then dissolved in $CH_2Cl_2$ (100 mL) and washed with sat. $NaHCO_3$ (100 mL). Concentration of the organic layers gave a residue which was purified by column chromatography (silica gel) using methanol (2%) in chloroform as eluant. The resulting pure product was precipitated from $CH_2Cl_2$ with ether and hexane and the off-white powder dried in vacuo at room temperature. Yield 115.8 mg (0.222 mmol, 44%). mp (dec.) 134–146. TLC (10% MeOH/CHCl$_3$)$R_f$ 0.53. $^1H$—NMR (CDCl$_3$) δ2.32 (s, 6H, N',N'-dimethyls), 2.54 (t, 2H, $CH_2NMe_2$) 3.52 (q, 2H, $NCH_2C$), 3.69 (m, 4H, chloroethyl), 3.83 (m, 4H, chloroethyl), 4.05 (s, 3H, imidazole-1-methyl), 4.09 (s, 6H, imidazole-1-methyl), 6.76 (d, 2H, phenyl), 7.43 (s, 1H, imidazole), 7.49 s, 1H, imidazole), 7.60 (br s, 1H, NH), 7.61 (s, 1H, imidazole), 7.87 (d, 1H, phenyl), 8.36 (s, 1H, NH), 9.30 (s, 1H, NH), 9.33 (s, 1H, NH). $^{13}C$—NMR (CDCl$_3$): δ35.6, 36.6, 40.1, 5.2, 53.3, 57.9, 111.3, 122.0, 129.2, 135.4, 135.7, 136.8, 146.0, 146.6, 149.2, 155.8, 159.1, 159.2, 170.5. IR (Nujol): υ3440, 1665, 1605, 1436 cm$^{-1}$. UV (ethanol) λmax 204, 310 nm. MS (FAB, NBA) m/z (relative intensity) 702 (M+H+, 10).

Anal. calcd. for $C_{30}H_{38}Cl_2N_{12}O_4 \cdot 3H_2O$: C, 47.69; H, 5.83.

Observed: C, 47.59; H, 5.46.

EXAMPLE 4

Synthesis of N-(N',N'-dimethylaminoethyl)-1-methyl-4-{1-methyl-4-[4-(4,4-bis-(2-chloroethyl)aminobenzylamino)-1-methylimidazole-2-carboxamido]imidazole-2-carboxamido}imidazole-2-carboxamide (Compound 8)

A solution of N-(N',N'-dimethylaminoethyl)-1-methyl-4-{1-methyl-4-[1-methyl-4-aminoimidazole-2-carboxamido]imidazole-2-carboxamido}imidazole-2-carboxamide (205 mg, 0.42 mmol) and p-N,N-bis(2-chloroethyl)aminobenzaldehyde (103 mg, 0.420 mmol) were suspended in dry acetonitrile (40 mL) and the reaction mixture was allowed to stir at room temperature under a drying tube until TLC analysis indicated that all of the starting materials were gone (22 h). At that time sodium borohydride (24.5 mg, 0.648 mol) was added to the reaction mixture and it was allowed to stir at room temperature for an addition 5 h. After TLC analysis indicated that all of the starting material was gone, water (20 mL) was added and the acetonitrile was removed under reduced pressure. The aqueous phase was extracted with $CH_2Cl_2$ (75 mL, 3x). The organic layers were combined, dried ($Na_2SO_4$), and the concentrated to a yellow foamy solid which was purified by column chromatography (silica gel) using a stepwise gradient of methanol (1–3%) in chloroform as eluant. The product was recrystallized from $CH_2Cl_2$ with ether and hexane and dried in vacuo at room temperature to yield an off-white powder Yield 14.1 mg (0.021 mmol, 5%). mp (dec) 110°–122° C. without melting. TLC (10% MeOH/CHCl$_3$)$R_f$ 0.37. $^1H$—NMR (CDCl$_3$): δ2.29 (s, 6H, N',N'-dimethyl), 2.52 (t, 2H, $CH_2NMe_2$), 3.46 (q, 2H, $NCH_2C$), 3.65 (m, 4H, chloroethyl), 3.70 (m, 4H, chloroethyl), 3.99 (s, 3H, imidazole-1-methyl), 4.02 (s, 3H, imidazole-1-methyl), 4.06 (s, 3H, imidazole-1-methyl), 4.14 (s, 2H, benzyl), 6.17 (s, 1H, imidazole), 6.65 (d, 2H, phenyl), 7.08 (br s, 1H, amine-NH), 7.26 (d, 2H, phenyl), 7.40 (s, 1H, imidazole), 7.43 (s, 1H, imidazole), 7.63 (br t, 1H, NH), 9.33 (br s, 1H, NH), 9.40 (br s, 1H, NH). IR(CHCl$_3$): υ3382, 3012, 1716, 1667, 1570, 1537, 1475 cm$^{-1}$. UV (ethanol): λmax 206 (ε 63848 cm$^{-1}$M$^{-1}$), 262 (ε7598 cm$^{-1}$M$^{-1}$), 308 nm (ε8219 cm$^{-1}$M$^{-1}$). MS (FAB, TFA-NBA) m/z relative intensity 688 (M+, 1), 689 (M+H+, 1). HRMS (FAB, TFA-NBA) for $C_{30}H_{40}N_{12}O_3Cl_2$ calcd. 688.2729. Observed 688.2735.

EXAMPLE 5

Synthesis of N-(N',N'-dimethylaminoethyl)-1-methyl-4-{4-[4,4-bis(2-chloroethyl)aminophenyl-1-butanamido]-1-methylimidazole-2-carboxamido}imidazole-2-carboxamide (Compound 9)

4-[p-Bis[2-chloroethylamino)phenyl]butyric chloride was prepared by dissolving 4-[p-Bis[2-chloroethyl]amino)-phenyl]butyric acid (159 mg, 0.523 mmol) in THF (5 mL) and oxalyl chloride (3 mL) and warming to mild reflux under a drying tube for 1.75 h. The excess oxalyl chloride and solvent were then removed under reduced pressure and the residue coevaporated with dry $CH_2Cl_2$ (5 mL, twice). The above acid chloride dissolved in dry $CH_2Cl_2$ (10 mL) was added dropwise to a chilled (0° C., ice bath) and stirring solution of N-(N',N'-dimethylaminoethyl)-1-methyl-4-[1-methyl-4-aminoimidazole-2-carboxamido]-imidazole-2-carboxamide (please provide amount) in dry $CH_2Cl_2$ (20 mL) with dry triethylamine (145 μL, 1.04 mmol) under an atmosphere of argon. The reaction mixture was kept at 0° C. for an addition 15 minutes and then allowed to stir at room temperature (22.5 h). After TLC analysis indicated that all of the starting material was gone, the reaction was concentrated under reduced pressure to an orange foam. The crude solid was purified by column chromatography (silica gel) with a methanol gradient (1%, then 1% increase every 100 mL) in chloroform as eluent. The resulting solid was washed with water and washed with ether/hexane to give the product as orange needles which was dried in vacuo at room temperature. Yield 61.2 mg (0.123 mmol, 23.5%): mp 101° C. (dec); TLC (10% MeOH/CHCl$_3$)$R_f$0.22; $^1H$—NMR (CDCl$_3$) δ2.02 (m, 2H, $CCH_2C$ butanamido), 2.49 (t, 2H, $CCH_2NMe_2$), 2.62 (t, 2H, $CCCH_2$ butanamido), 2.66 (t, 2H, $CH_2CC$ butanamido), 2.78 (s, 6H, N',N'-dimethyls), 3.20 (m, 2H, $NCH_2CNMe_2$), 3.62 (t, 4H, $ClCCH_2$), 3.69 (t, 4H, $ClCH_2$), 3.98 (s, 3H, imidazole-1-methyl), 4.00 (s, 3H, imidazole-1-methyl), 6.62 (d, 8.7, 2H, phenyl), 7.10 (d, 8.7, 2H, phenyl), 7.38 (s, 1H, imidazole), 7.42 (s, 1H, imidazole), 8.51 (br s, 1H, NH), 8.83 (br s, 1H, NH), 9.34 (br s, 1H, NH); IR (Nujol) 3413, 2974, 1664, 1541, 1477, 1397, 1173, 1034, 779 cm$^{-1}$; UV (H$_2$O) λmax 260 nm (ε5236 cm$^{-1}$M$^{-1}$), 306 nm (ε5813 cm$^{-1}$M$^{-1}$); MS (FAB, Thioglycerol) m/z (relative intensity): 620 (M +H$^+$); H.R.M.S (FAB, Thioglycerol) calcd. for C$_{28}$H$_{40}$N$_9$O$_3$Cl$_2$ 620.06336. Observed 620.0638.

EXAMPLE 6

Synthesis of N-(N',N'-dimethylaminoethyl)-1-methyl-4-{1-methyl-4-[4-(4,4-bis(2-chloroethyl)aminophenyl-1-butanamido)-1-methylimidazole-2-carboxamido]imidazole-2-carboxamido}imidazole-2-carboxamide (Compound 10)

This procedure is similar to the synthesis of Compound 14 except the amine used was N-(N',N'-dimethylaminoethyl)-1-methyl-4-{1-methyl-4[1-methyl-4-aminoimidazole-2-carboxamido]imidazole-2-carboxamido}imidazole-2-carboxamide. The product was obtained as orange needles. Yield 58.0 mg 0.0781 mmol, 31.2%): mp 108° C. (dec); TLC (10% MeOH/CHCl$_3$R$_f$0.18; $^1$H—NMR (CDCl$_3$) δ2.02 (m, 2H, CCH$_2$C butanamido), 2.50 (m, 2H, CH$_2$CC butanamido), 2.58 (m, 6.4, 2H, CCH$_2$NMe$_2$), 2.62 (m, 2H, CCCH$_2$ butanamido), 2.78 (s, 3H, N',N'-dimethyl), 2.84 (s, 3H, N',N'-dimethyl), 3.29 (m, 2H, NCH$_2$CNMe$_2$), 3.62 (t, 6.9, 4H, ClCCH$_2$), 3.70 (t, 6.9, 4H, ClCH$_2$), 3.97 (s, 3H, imidazole-1-methyl), 4.00 (s, 6H, imidazole-1-methyl), 6.62 (d, 2H, phenyl), 7.07 (d, 2H, phenyl), 7.32 (s, 1H, imidazole), 7.36 (s, 1H, imidazole), 7.42 (s, 1H, imidazole), 8.38 (br s, 1H, NH), 8.46 (br s, 1H, NH), 9.54 (br s, 1H, NH), 9.79 (br s, 1H, NH); IR (Nujol) υ3369, 2931, 1664, 1536, 1466, 1023, 779 cm$^{-1}$; UV (H$_2$O) λmax 306 nm (ε1.29×10$^4$ cm$^{-1}$M$^{-1}$); MS (FAB, Thioglycerol) m/z (relative intensity) 743 (M +H$^+$, 100); HRMS (FAB, Thioglycerol) calcd. for C$_{33}$H$_{45}$N$_{12}$O$_4$ Cl$_2$ 743.3070, Observed 743.3066.

EXAMPLE 7

Synthesis of N-(N',N'-dimethylaminoethyl)-1-methyl-4-[4-(chloroacetamido)-1-methylimidazole-2-carboxamido)imidazole-2-carboxamide (Compound 11)

A solution of N-(N',N'-dimethylaminoethyl)-1-methyl-4-[1-methyl-4-aminoimidazole-2-carboxamido]-imidazole-2-carboxamide (180 mg, 0.54 mmole) in dry CH$_2$Cl$_2$ (15 mL) and dry triethylamine (84 μL, 0.60 mmol) under an atmosphere of argon was cooled to −20° C. (CCl$_4$/liq N$_2$ bath), and a solution of chloroacetyl chloride (48 μL, 0.603 mmol), dissolved in dry CH$_2$Cl$_2$ (3 mL), was added dropwise. The reaction mixture was kept at −20° C. for an additional 15 minutes and then allowed to stir overnight at room temperature (17 h). The reaction was concentrated to a light yellow foam and then was dissolved in water (40 mL) and saturated NaHCO$_3$ (20 mL). The aqueous phase was extracted with CH$_2$Cl$_2$ (100 mL, 3x). The combined organic layers were then washed with sat. NaCl (100 mL), dried (Na$_2$SO$_4$) and concentrated to a yellow oil which was purified by column chromatography (silica gel) using a stepwise gradient of methanol (1–7%) in chloroform as eluent. The resulting pure product was precipitated from CH$_2$Cl$_2$ with ether and hexane, and the off-white powder was dried in vacuo at room temperature. Yield: 55.3 mg (0.14 mmol, 25%); mp 206° C. (dec); TLC (10% MeOH/CHCl$_3$)R$_f$ 0.27. $^1$H NMR (CDCl$_3$) δ2.25 (s, 6H, N',N'-dimethyls), 2.50 (t, 6.1, 2H, CH$_2$NMe$_2$), 3.50 (q, 6.1, 2H, NCH$_2$C), 4.05 (s, 3H, imidazole-1-methyl), 4.10 (s, 3H, imidazole-1-methyl), 4.20 (s, 2H, chloroacetyl), 7.35 (s, 1H, imidazole), 7.45 (s, 1H, imidazole), 7.55 (t, 6.1, 1H, NH), 8.70 (br s, 1H, NH), 9.25 (br s, 1H, NH); IR(Nujol) υ3382, 1663, 1535 cm$^{-1}$; Uv (EtOH) εmax 208, 304 nm; MS (FAB, TFA-NBA) m/e relative intensity) 411 (M+H$^+$, 1), 307 (38). Anal. (C$_{16}$H$_{23}$ClN$_8$O$_3$.2H$_2$O) C, H.

EXAMPLE 8

Synthesis of N-(N',N'-dimethylaminoethyl)-1-methyl-4-[4-(bromoacetamido)-1-methylimidazole-2-carboxamido]imidazole-2-carboxamide (Compound 12)

The procedure is similar to that for the synthesis of Compound 16 except bromoacetyl chloride was used in place of chloroacetyl chloride. The resulting pure product was precipitated from CH$_2$Cl$_2$ with ether and hexane, and the yellow powder was dried in vacuo at room temperature. Yield: 13.8 mg (0.030 mmol, 5%); mp 197°–201° C. (dec); TLC (10% MeOH/CHCl3)R$_f$0.26; $^1$H NMR (CDCl$_3$) δ2.25 (s, 6H, N',N'-dimethyls), 2.51 (t, 5.7, 2H, CH$_2$NMe$_2$), 3.47 (q, 5.7, 2H, NCH$_2$C), 4.04 (s, 3H, imidazole-1-methyl), 4.07 (s, 3H, imidazole-1-methyl), 4.20 (s, 2H, bromoacetyl), 7.40 (s, 1H, imidazole), 7.45 (s, 1H, imidazole), 7.55 (t, 5.7, 1H, NH), 8.65 (br s, 1H, NH), 9.23 (br s, 1H, NH); IR(Nujol) υ3420, 1664, 1534 cm$^{-1}$; Uv (ethanol) εmax 206, 304 nm; MS (FAB, NBA) m/e (relative intensity) 455(M+H$^+$, 2), 338(10), 307(20). HRMS (FAB-NBA) m/e 455.1164 (C$_{16}$H$_{24}$N$_8$O$_3$Br requires 455.1157).

EXAMPLE 9

The ethidium displacement assay is based on the fact that ethidium binding to DNA causes a large (approximately 25 fold) florescence enhancement as a result of the hydrophobic environment surrounding the ethidium molecule. Displacement of ethidium results in decreased fluorescence, and thus binding constants of drugs to DNA can be estimated and compared by measuring the loss of fluorescence as a function of added drug. The drug concentration which produces 50% inhibition of florescence is approximately inversely proportional to the apparent binding constant. Since the ethidium displacement assay provides relative values of K$_{app}$ rather than absolute numbers, the data are compared to the K$_{app}$ values for distamycin, which is known to bind the minor groove of DNA and to exhibit preference for (AT)$_5$ sequences.

The apparent binding constants for T4 coliphage DNA are an indicator of the minor groove selectivity of the compounds of the present invention. The major groove of T4 coliphage DNA is blocked by α-glycosylation of the 5-hydroxymethylcytidine residues; therefore, the non-intercalating agents that bind to T4 coliphage DNA must interact in the minor groove [Lown (1982) *Acc. Chem. Res.*, 15, 381].

The relative DNA binding constants (K$_{app}$) of distamycin and Compounds 6–10 to calf thymus DNA, T4 coliphage DNA, poly(dAdT) and poly(dGdC) were determined using the ethidium displacement assay (Morgan et al., 1979). The K$_{app}$ of ethidium bromide (Debart et al., 1989) is included for comparison. 25 μL of a 2A$_{260}$ DNA solution was added to 2 mL of ethidium bromide buffer (250 μL of 1.3 mM ethidium bromidestock, 314.9 mg Tris-HCl, 60.8 mg Tris base and 930/mg of Na$_2$EDTA.2H$_2$O in 250 ml H$_2$O) pH 7.4 and the maximum fluorescence was measured (excitation wavelength=546 nm, emission wavelength=600 nm) at ambient temperature.

DNA solutions of $2A_{260}$ were prepared as follows: T4 coliphage DNA: 10 units of DNA were dissolved in 1 mL of 10 mM sodium phosphate (pH 7.1) and 0.25 mM EDTA buffer to give a $10A_{260}$ solution. 0.3 mL of the stock solution were diluted to 1.5 mL with 10 mM sodium phosphate (pH 7.1) and 0.25 mM EDTA buffer to give a $2A_{260}$ solution. Calf thymus DNA: 100 units of DNA were dissolved in 5 mL of 10 mM sodium phosphate (pH 7.1) and 0.25 mM EDTA buffer to give a $20A_{260}$ solution. 1.5 mL of the stock solution were diluted to 15 mL with 10 mM sodium phosphate (pH 7.1) and 0.25 mM EDTA buffer to give a $2A_{260}$ solution. Poly(dA-dT) and Poly(dG-dC) DNA: 100 units of DNA were dissolved in 10 mL of 10 mM sodium phosphate pH 7.1) and 0.25 mM EDTA buffer to give a $10A_{260}$ solution. 3 mL of the stock solution were diluted to 15 mL with 10 mM sodium phosphate (pH 7.1) and 0.25 mM EDTA buffer to give a $2A_{260}$ solution.

Aliquots of 10 mM stock drug solution (1 mg of drug to be tested was dissolved with 1 mole equivalent of 0.1M HCl, and then diluted with appropriate volume of distilled water to make a 10 mM solution) were then added to the fluorescing solution and the florescence measured after each addition until a 50% reduction of fluorescence occurred. If the 10 mM stock solution lowered the % fluorescence too quickly, the stock solution was further diluted to 1 mM prior to titration. The apparent binding constant was then calculated from this equation: $K_{EtBr}[EtBr] = K_{app}[drug]$, where [drug] = the concentration of drug at a 50% reduction of fluorescence and $K_{EtBr}[1 \times 10^7 M^{-1}$ for calf thymus and coliphage T4 DNA[18], $9.5 \times 10^6 M^{-1}$ for poly(dA.dT)[30], and $9.9 \times 10^6 M^{-1}$ for poly(dG.dC)[30] and [EtBr] were known. The concentration of ethidium bromide was 1.3 $\mu$M. The $K_{app}$ values are shown in Table I. In a separate experiment, the $K_{app}$ of Compound 5 for calf thymus DNA and poly[dGdC] were determined to be $0.3 \times 10^5 M^{-1}$ and $2.6 \times 10^5 M^{-1}$, respectively. The error in these measurements is $\pm 0.1 \times 10^{-4} M^{-1}$. The above data demonstrate that the imidazole- and C-terminus-modified analogs can bend to the DNAs studied.

TABLE I

| Association Constants ($K_{app}$, $\pm 0.02 \times 10^5 M^{-1}$) of Compounds 6–10 with Polynucleotides | | | | |
|---|---|---|---|---|
| Compound | calf thymus | T4 | poly(dAdT) | poly(dGdC) |
| EtBr | 100[a] | 100[b] | 95[b] | 99[b] |
| Distamycin | 7.74 | 6.4 | 348 | 2.03 |
| 6 | 4.56 | 2.36 | 4.75 | 4.55 |
| 7 | 5.91 | 1.68 | 9.5 | 4.95 |
| 8 | 4.73 | 1.93 | 4.57 | 3.39 |
| 9 | 0.64 | 0.75 | 0.54 | 0.76 |
| 10 | 0.22 | 0.19 | 0.13 | 0.16 |

[a]Morgan et al. (1979) Nucl. Acids Res. 7, 547.
[b]Debart et al. (1989) J. Med. Chem. 32, 104.

EXAMPLE 10

UV-DIALYSIS STUDY 0.5 mL of $2A_{260}$ calf thymus DNA was diluted to 2 mL with 10 mM sodium phosphate and 0.25 mM EDTA buffer, pH 7.1. Four aliquots (3 $\mu$L each) of a 1 mM stock drug solution in distilled water were added to the DNA solution and a UV absorption spectrum (300–320) was recorded after each addition. The drug/DNA solution was incubated for 24 h at room temperature and another UV spectrum was recorded. The drug/DNA solution was then transferred into a dialysis bag and the dialysis bag was suspended in 30 mL of 10 mM sodium phosphate and 0.25 mM EDTA buffer, pH, 7.1, at room temperature. After 20–26 hours, the TLC spectrum of 2 mL of the buffer outside the dialysis bag was recorded. The absorbance of the drug peak was converted to concentration by the Beer-Lambert equation, and the data was presented as percent initial concentration. Under these conditions, substantial amounts of Compounds 6 (55±5%), 7 (45±5%), 8 (85±5%) and 10 (100±5%) are retained in the dialysis bag, while only 29±5% of a formamido analog[1] is retained.

[1] N-(N',N'-dimethylaminoethyl)-1-methyl-4-{1-methyl-4-[4-formamido-2-methylimidazole-2-carboxamido]imidazole-2-carboxamido}imidazole-2-carboxamide.

EXAMPLE 11

The DNA binding properties of the present compounds were assessed by circular dichroism (CD) titration experiments. Methods for CD titration can be found, for example, in Zimmer et al. (1986) Prog. Biophys. Molec. Biol 47, 31. The conformation of DNA can be readily determined by CD experiments, and for B-DNA, characteristic positive and negative Cotton effects are observed at 260 and 245 nm, respectively. However, interaction of achiral molecules with the DNA can cause changes in the CD spectrum, such as the appearance of ligand-induced bands and/or alteration in the original CD spectrum Thus, changes in the CD spectra of DNA induced by titration with the compounds of the present invention further evidences the DNA binding ability of the present compounds, since the compounds alone do not exhibit any CD spectra.

The interaction of Compounds 6–10 to a number of DNAs [calf thymus, poly(dA dT) and poly(dG dC)] were analyzed by CD titration studies. All the CD titration experiments were performed using identical procedures, concentrations of DNA, and increments of drug:DNA ratios (or 'r', i.e. moles of drug to moles of DNA base pairs). Therefore, the differences observed in the CD spectra for the titration of each of the compounds to the polydeoxynucleotides may be directly compared to reflect their DNA binding properties.

All experiments were performed with a continuous flow of nitrogen purging the polarimeter. A 1 mm path length jacketed cell was used and all experiments were done at room temperature. Initially, DNA [0.02 $\mu$ moles (base pairs), 130 $\mu$L] was placed in the cell and the spectrum of the DNA alone was collected. Aliquots of drug were added and the spectra collected. The drug solutions were 1 mM and amounts of the drug added correspond to a drug to base pair ratio of 0.05, 0.10, 0.15, 0.20, 0.25, 0.30, 0.40, 0.50, 0.60, 0.80, 1.00. The scan parameters were set and standard for all experiments. The spectra were collected from 400 nm to 200 nm. The sensitivity was set at 1 mdeg and the scan speed was set at 20 nm per minute. Three scans were accumulated and automatically averaged by the computer. The $\lambda_{max}$ and ellipticity (mdeg) for each spectrum were collected from the raw scans and the final plots were smoothed by the noise reduction program on the computer. The results show that Compounds 6 and 7 bind to the DNAs as indicated by the appearance of drug-induced CD bands at about 290–340 nm, because the drugs alone do not exhibit any CD spectra. The induced CD band is presumably due to the uv absorption $\pi$ to $\pi^*$ transition of the drug in the drug:DNA complex. In the above CD titration studies, the appearance of the positive and negative bands at ~270 and ~250 nm suggest that the conformation of the DNA duplex in the drug:DNA complexes remains in the B-form. Therefore interaction of these drugs with DNA causes only minor conformational changes in the double helix. Titration of Compound 6 to poly(dA.dT) gave rise to a positive band at 350 nm (1.8 mdeg, r'=0.2, a negative band at 310 nm (0.4 mdeg, r'=0.2) and an isobestic point at 315 nm. At equimolar concentration of the drug, the compound produced a negative band at 330 nm (0.7 mdeg, r'=0.2) and an isobestic point at 297 nm when titrated into poly(dG.dC). Titration of Compound 6 to calf thymus DNA revealed that at a low concentration of the drug a weak positive band at 340 nm (0.8 mdeg, r'=0.2) a negative band at 310 nm (0.2 mdeg, r'=0.2), and an isobestic point at 320 were observed. However at higher drug concentrations (r'>0.4) the positive band at 340 nm disappeared, and the negative band at 315 nm intensified (to ~3 mdeg) dramatically indicating a different mode of binding of the drug to the DNA. From the plot of induced ellipticity of the titration of the drug to calf thymus DNA, a saturation point was seen at r'~0.25 suggesting that the binding site size is about four base pairs. Titration of Compound 8 to poly(dA.dT) with r' up to ~1.0 did not produce any changes in the CD spectrum; however, with poly(dG.dC), a new positive Cotton effect shoulder appeared at 288 nm, thus suggesting the formation of 8:DNA complex because Compound 8 alone does not exhibit a CD spectrum.

Titration of Compound 9 to the three polydeoxyribonucleotides did not produce any notable changes in the CD spectra even at the r' (moles of drug to DNA base pairs) value of 0.8. This is probably due to low DNA binding affinity as a result of fewer amido-NHs and van der Waals contacts compared to distamycin. Addition of the triimidazole chlorambucil conjugate Compound 10 to poly(dA.dT) and poly(dG.dC) produced weak drug induced bands on the CD spectra. At equimolar titration of this compound to the DNAs, negative Cotton effect bands at 315 nm (−0.8 mdeg and −1.0 mdeg) at the r' value of 1.2 were observed. The induced CD band is presumably due to the UV absorption $\pi$ to $\pi^*$ transition of the drug in the drug:DNA complex. These data suggest that Compound 10 binds more strongly to GC rich sequences of DNA.

Titration of Compound 7 to poly(dA.dT) caused minor changes in the CD spectrum suggesting that there was minimal interaction of the drug with this DNA even when the concentration of the drug was raised to r'=1.0. However, titration of this drug to poly(dG dC) produced a strong negative cotton effect at 333 nm (1 mdeg, r'=0.2) along with a slight decrease in the positive band at 275 nm, and an isobestic point at 283 nm was observed. It should be noted that the ellipticity of the induced-CD band(s) increases with additional increments of drug. Finally, titration of Compound 7 to calf thymus DNA produced a weak negative band at 335 nm (0.5 mdeg, r'=0.2), a decrease in the positive band at 285 nm, and an isobestic point at 300 nm was recorded. The binding site size of Compound 7 to calf thymus DNA at saturation was found to be four base pairs (i.e. r'~0.25). The above data obtained from titration of the drugs into the three DNAs provide evidence that (i) they bind strongly to DNA with a significant binding site size; (ii) these compounds show significant preference for GC rich sequences as indicated by the larger induced band for poly(dG.dC) than poly(dA.dT) at equal drug concentrations.

EXAMPLE 12

The ability of the compounds of the present invention to inhibit the growth of human chronic myelogenous leukemic K562 cells was determined as follows.

The K562 human chronic myeloid leukemia cells were maintained in RPMl 1640 medium supplemented with 10% fetal calf serum and 2 mM glutamine at 37° C. in a humidified atmosphere containing 5% $CO_2$ and were incubated with a specified dose of drug for 1 hour at 37° C. in the dark. The incubation was terminated by centrifugation (5 minutes, 300 g) and the cells washed once with drug-free medium.

Following the appropriate drug treatment, the cells were transferred to 96-well microtiter plates, $10^4$ cells per well, 8 wells per sample. Plates were then kept in the dark at 37° C. in a humidified atmosphere containing 5% $CO_2$. The viability assay is based in the ability of viable cells to reduce a yellow soluble tetrazolium salt, 3-4,5-dimethylthiazol-2,5-diphenyltetrazolium bromide MTT, Sigma Chemical Co.) to an insoluble purple formazan precipitate (Carmichael et al., 1987). Following incubation of the plates of 5–6 days (to allow control cells to increase in the number by 10 fold) 20 µL of a 5 mg/mL solution of MTT in phosphate buffered saline was added to each well and the plates further incubated for 5 h. The plates were then centrifuged for 5 minutes at 300 g and the bulk of the medium pipetted from the cell pellet leaving 10–20 µL per well. 200 µL DMSO was added to each well and the samples agitated to ensure complete mixing. The optical density was then read at a wavelength of 550 nm on a Titertek Multiscan ELISA plate reader and the dose-response curve constructed. For each curve, an $IC_{50}$ value was read as the dose required to reduce the final optical density to 50% of the control value.

The $IC_{50}$ values for compounds of the present invention are presented in Table II. Analogs in which the N-terminal alkylating group was replaced by a formyl group (Compounds 13, 14 and 15) showed no activity against the growth of K562 cells.

TABLE II

| In Vitro Cytotoxicity Against Human Chronic Leukemia K562 Cells | |
|---|---|
| Compound | $IC_{50}$ (µM) |
| 6 | 12.5 |
| 7 | 0.30 |
| 8 | 0.85 |
| 9 | 70 |
| 10 | 28 |
| 11 | 350 |
| 12 | 400 |
| 13[2] | >500 |
| 14[3] | >500 |
| 15[4] | >500 |

[2]N-(N',N'-dimethylamino)-1-methyl-4-[4-formamido-1-methylimidazole-2-carboxamido]-imidazole-2-carboxamide.
[3]N-(N',N'-dimethylaminoethyl)-1-methyl-4-[4-formamido-1-methylimidazole-2-carboxamido]-imidazole-2-carboxamide.
[4]N-(N',N'-dimethylaminoethyl)-1-methyl-4-{1-methyl-4-[4-formamido-2-methylimidazole-2-carboxamido]imidazole-2-carboxamido}imidazole-2-carboxamide.

EXAMPLE 13

Compounds 6, 7, 9 and 10 were tested for cytotoxic properties by the National Cancer Institute, Bethesda, Md. The anticancer drug screen utilized a panel of 60 human tumor cell lines organized into subpanels representing leukemia, melanoma, and cancers of the lung, colon, kidney, ovary and central nervous system and is described by Monks et al. (1991) *Journal of the National Cancer Institute* 83, 757, which is incorporated herein by reference.

Cell lines were inoculated onto microtiter plates and preincubated for 24-28 hours. 100 μL aliquots of each compound were added to the appropriate microtiter plate wells in each of five 10-fold dilutions starting from a maximum concentration of $10^{-4}$M in water or DMSO. Cultures were then incubated for an additional 48 hours. Cells were then fixed in situ, followed by staining with sulforhodamine B (SRB), which binds to basic amino acids of cellular macromolecules. The solubilized stain was measured spectrophotometrically to determine relative cell growth or viability in treated and untreated cells. Optical density data were calculated as described in Monks et al. Cytotoxicity data is presented in Tables 3 and 4. The monoimidazole analogs of Compounds 6, 7, 9 and 10 and the formamido analog corresponding to Compounds 7 and 10 are devoid of activity against the panel of cancer cell lines in Table III.

TABLE III

Cytotoxicity ($IC_{50}$ values in $10^{-6}$ M) of Compound 6 and 7 Against Cultured Human Tumor Cell Lines

| Cell Line | 6 | 6[a] | 7 | 7[a] |
|---|---|---|---|---|
| Leukemia | | | | |
| CCRF-CEM | 10.9 | 40.3 | 1.52 | |
| HL-60 (TB) | 7.84 | 7.93 | 0.72 | |
| K-562 | 17.2 | 12.3 | 0.58 | |
| Molt-4 | 18.1 | >100 | 0.98 | |
| RPMI-8226 | 30.5 | 39.4 | | |
| SR | 10.4 | >100 | 0.91 | |
| Non-Small Cell Lung Cancer | | | | |
| A549/ATCC | 58.8 | 38.4 | 5.64 | 4.12 |
| EKVX | 47.5 | 38.0 | 0.88 | 1.70 |
| HOP-18 | | 10.2 | | |
| HOP-62 | 52.3 | 50.6 | 1.17 | |
| HOP-92 | | 42.7 | | 3.33 |
| NCI-H226 | 62.2 | 61.3 | | 5.54 |
| NCI-H23 | 47.1 | 43.6 | 0.96 | 2.35 |
| NCI-H322M | 40.5 | 51.7 | 2.39 | 1.97 |
| NCI-H460 | 46.1 | 35.1 | 5.67 | 4.12 |
| NCI-H522 | 6.98 | 5.74 | 4.41 | 0.42 |
| LXFL529 | 13.2 | 34.8 | | 0.54 |
| Small Cell Lung Cancer | | | | |
| DMS-114 | 5.83 | 4.99 | | 0.54 |
| DMS-273 | | 31.3 | | 0.99 |
| Colon Cancer | | | | |
| COLO-205 | 5.88 | 7.39 | 0.97 | 0.56 |
| DLD-1 | 46.6 | 55.5 | 4.34 | |
| HCC-2998 | 33.7 | 8.14 | 0.68 | 0.89 |
| HCT-116 | 6.54 | 6.71 | | |
| HCT-15 | 40.5 | 43.2 | >10 | >100 |
| HT29 | 5.90 | 27.4 | 2.30 | 1.97 |
| KM12 | 47.0 | 31.6 | 0.96 | 0.75 |
| KM20L2 | 6.77 | 20.1 | 7.92 | |
| SW-620 | 9.95 | 12.0 | 0.79 | 0.63 |
| CNS Cancer | | | | |
| SF-268 | 50.0 | 9.21 | 0.77 | |
| SF-295 | 43.6 | 33.2 | 4.10 | |
| SF-539 | 6.97 | 57.3 | | 0.59 |
| SNB-19 | 43.7 | 32.4 | >100 | |
| SNB-75 | 41.0 | 41.7 | 0.61 | |
| SNB-78 | 67.2 | 78.9 | | |
| U251 | 6.73 | 5.80 | | 0.50 |
| XF498 | | 25.2 | 0.62 | 0.65 |
| Melanoma | | | | |
| LOX IMV1 | | 7.47 | 0.89 | 4.51 |
| MALME-3M | 6.14 | 64.3 | 2.63 | 4.34 |

TABLE III-continued

Cytotoxicity ($IC_{50}$ values in $10^{-6}$ M) of Compound 6 and 7 Against Cultured Human Tumor Cell Lines

| Cell Line | 6 | 6[a] | 7 | 7[a] |
|---|---|---|---|---|
| M14 | 5.92 | 5.81 | | 0.59 |
| M19-MEL | 5.64 | 5.65 | | 0.78 |
| SK-MEL-2 | 7.17 | 5.85 | 0.65 | |
| SK-MEL-28 | 5.69 | 5.78 | 0.91 | 0.64 |
| SK-MEL-5 | | 52.0 | 0.63 | |
| UACC-257 | 7.03 | 57.6 | | |
| UACC-62 | 7.61 | 59.7 | | |
| Ovarian Cancer | | | | |
| IGROV1 | 50.0 | 59.6 | | |
| OVCAR-3 | 56.0 | 56.7 | 0.72 | 0.62 |
| OVCAR-4 | 34.2 | 14.3 | 0.61 | 0.50 |
| OVCAR-5 | 45.7 | 51.3 | 6.13 | 5.24 |
| OVCAR-8 | 45.3 | 20.8 | | |
| SK-OV-3 | 52.9 | 6.18 | 0.83 | 0.48 |
| Renal Cancer | | | | |
| 786-0 | 25.4 | 6.98 | | 0.51 |
| A498 | 40.6 | 66.0 | 7.76 | |
| ACHN | 54.2 | 46.9 | 7.05 | 4.92 |
| CAKI-1 | 51.9 | 59.7 | >100 | |
| RXF-393 | 50.3 | 44.3 | 0.66 | |
| RXR-631 | 6.61 | 9.95 | 5.97 | |
| SN12C | 15.6 | 39.9 | | 0.61 |
| TK-10 | 59.9 | 56.2 | 4.20 | 3.51 |
| VO-31 | 59.2 | 57.9 | >100 | 96.6 |

[a]Results of identical assay on subsequent test date.

TABLE IV

Cytotoxicity ($IC_{50}$ values in $10^{-6}$ M) of Compounds 9 and 10 Against Cultured Human Tumor Cell Lines

| Cell Line | 9 | 10 |
|---|---|---|
| Leukemia | | |
| CCRF-DEM | | 9.67 |
| HL-60(TB) | 43.8 | 7.89 |
| K-562 | 54.2 | 7.05 |
| Molt-4 | 71.3 | 3.19 |
| RPMI-8226 | | 9.50 |
| Non-Small Cell Lung Cancer | | |
| A549/ATCC | 78.5 | 10.7 |
| EKVX | | 87.8 |
| HOP-62 | 75.5 | 44.0 |
| NCI-H226 | 47.9 | 67.5 |
| NCI-H23 | 67.3 | 34.8 |
| NCI-H322M | 77.6 | 23.9 |
| NCI-H460 | 43.5 | 6.13 |
| NCI-H522 | 86.6 | 6.77 |
| Small Cell Lung Cancer | | |
| DMS-114 | | 7.49 |
| DMS-273 | 42.7 | 6.78 |
| Colon Cancer | | |
| COLO-205 | 81.6 | 11.4 |
| DLD-1 | | 42.2 |
| HCC-2998 | 55.1 | 38.5 |
| HCT-116 | 50.2 | 5.76 |
| HCT-15 | 61.3 | 45.3 |
| HT29 | | 51.0 |
| KM12 | 60.9 | 24.1 |
| KM20L2 | 53.4 | 8.63 |
| SW-620 | 77.3 | 9.30 |
| CNS Cancer | | |
| SF-268 | | 31.3 |
| SF-295 | 51.9 | 9.74 |
| SF-539 | 47.9 | 6.13 |
| SNB-78 | | 9.75 |
| U251 | 46.2 | 5.27 |
| XF498 | | 5.79 |
| Melanoma | | |
| LOX IMVI | 49.5 | 6.44 |
| MALME-3M | 56.3 | 52.7 |

What is claimed:

1. A compound of the Formula (I)

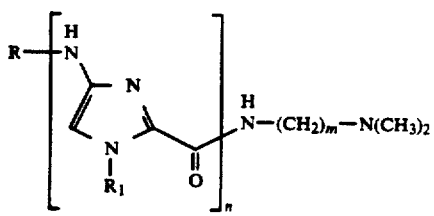

wherein
 m is 0 to 4;
 n is 2 to 4;
 each $R_1$ is the same or different and is hydrogen or $C_1$–$C_4$ alkyl; and R is a DNA alkylating moiety.

2. The compound of claim 1 wherein said DNA alkylating moiety is nitrogen mustard, nitrosourea, aziridine, methanesulfonate ester or epoxide.

3. The compound of claim 1 wherein
 R is
  —CO(CH$_2$)$_p$R$_3$;
  —CO(CH$_2$)$_p$CH(R$_3$)$_2$;
  —CO(CH$_2$)$_p$C(R$_3$)$_3$;
  —(CH$_2$)$_p$AN(R$_4$)$_2$; or
  —(CO)(CH$_2$)$_p$AN(R$_4$)$_2$,
 where p is 0–4; $R_3$ is halogen; A is a divalent ortho-, meta- or para-substituted phenyl group; and $R_4$ is $C_2$–$C_4$ alkyl 2-substituted by halogen.

4. The compound of claim 1 wherein $R_1$ is methyl.
5. The compound of claim 1 wherein m is 2.
6. The compound of claim 1 wherein n is 3.
7. The compound of claim 1 wherein R is —CO(CH$_2$)$_p$AN(R$_4$)$_2$ and $R_4$ is 2-chloroethyl.
8. The compound of claim 1 wherein R is —(CH$_2$)$_p$AN(R$_4$)$_2$ and $R_4$ is 2-chloroethyl.
9. The compound of claim 7 wherein $R_1$ is methyl, p is 0, A is para-substituted phenyl, and m is 2.
10. The compound of claim 9 wherein n is 2.
11. The compound of claim 9 wherein n is 3.
12. The compound of claim 1 wherein said compound is N-(N',N'-dimethylamino)-1-methyl-4-{4-[4,4-bis(2-chloroethyl)aminobenzamido]-1-methylimidazole-2-carboxamido}imidazole-2-carboxamide.
13. The compound of claim 1 wherein said compound is N-(N',N'-dimethylaminoethyl)-1-methyl-4-{4-[4,4-bis(2-chloroethyl)aminobenzamido]-1-methylimidazole-2-carboxamido}imidazole-2-carboxamide.
14. The compound of claim 1 wherein said compound is N-(N',N'-dimethylaminoethyl)-1-methyl-4-{1-methyl-4-[4-(4,4-bis-(2-chloroethyl)aminobenzamido)-1-methylimidazole-2-carboxamido]imidazole-2-carboxamido}imidazole-2-carboxamide.
15. The compound of claim 1 wherein said compound is N-(N',N'-dimethylaminoethyl)-1-methyl-4-{1-methyl-4-[4-(4,4-bis-(2-chloroethyl)aminobenzylamino)-1-methylimidazole-2-carboxamido]imidazole-2-carboxamido}imidazole-2-carboxamide.
16. The compound of claim 1 wherein said compound is N-(N',N'-dimethylaminoethyl)-1-methyl-4-{4-[4,4-bis(2-chloroethyl)aminophenyl-1-butanamido]-1-methylimidazole-2-carboxamido}imidazole-2-carboxamide.
17. The compound of claim 1 wherein said compound is N-(N',N'-dimethylaminoethyl)-1-methyl-4-{1-methyl-4-[4-(4,4-bis(2-chloroethyl)aminophenyl-1-butanamido)-1-methylimidazole-2-carboxamido]imidazole-2-carboxamido}imidazole-2-carboxamide.

18. The compound of claim 1 wherein said compound is N-(N',N'-dimethylaminoethyl)-1-methyl-4-[4-(chloroacetamido)-1-methylimidazole-2-carboxamido]imidazole-2-carboxamide.

19. The compound of claim 1 wherein said compound is N-(N',N'-dimethylaminoethyl)-1-methyl-4-[4-(bromoacetamido)-1-methylimidazole-2-carboxamido]imidazole-2-carboxamide.

20. A pharmaceutically acceptable salt of the compound of claim 1.

21. A method of treatment of cancer responsive to a therapeutically effective amount of a compound of the formula:

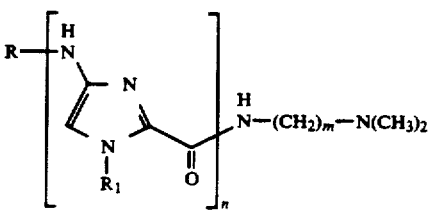

wherein
 m is 0 to 4;
 n is 2 to 4;
 each $R_1$ is the same or different and is hydrogen or $C_1$–$C_4$ alkyl; and R is a DNA alkylating moiety comprising administering to a patient a therapeutically effective amount of said compound.

22. The method of claim 21 wherein said DNA alkylating moiety is a nitrogen mustard, nitrosourea, aziridine, methanesulfonate ester or epoxide.

23. The method of claim 21 wherein
 R is
  —CO(CH$_2$)$_p$R$_3$;
  —CO(CH$_2$)$_p$CH(R$_3$)$_2$;
  —CO(CH$_2$)$_p$C(R$_3$)$_3$;
  —(CH$_2$)$_p$AN(R$_4$)$_2$; or
  —(CO)(CH$_2$)$_p$AN(R$_4$)$_2$,
 wherein p is 0–4; $R_3$ is halogen; A is a divalent ortho-, meta- or para-substituted phenyl group; and $R_4$ is $C_2$–$C_4$ alkyl 2-substituted by halogen.

24. The method of claim 21 wherein $R_1$ is methyl.
25. The method of claim 21 wherein m is 2.
26. The method of claim 21 wherein n is 3.
27. The method of claim 21 wherein R is —CO(CH$_2$)$_p$AN(R$_4$)$_2$ and $R_4$ is 2-chloroethyl.
28. The method of claim 21 wherein $R_1$ is —(CH$_2$)$_p$AN(R$_4$)$_2$ and $R_4$ is 2-chloroethyl.
29. The method of claim 27 wherein $R_1$ is methyl, p is 0, A is para-substituted phenyl, and m is 2.
30. The method of claim 29 wherein n is 2.
31. The method of claim 29 wherein n is 3.
32. The method of claim 21 wherein said compound is N-(N',N'-dimethylaminoethyl)-1-methyl-4-{4-[4,4-bis(2-chloroethyl)aminobenzamido]-1-methylimidazole-2-carboxamido}imidazole-2-carboxamide.
33. The method of claim 21 wherein said compound is N-(N',N'-dimethylaminoethyl)-1-methyl-4-{4-[4,4-bis(2-chloroethyl)aminobenzamido]-1-methylimidazole-2-carboxamido}imidazole-2-carboxamide.

34. The method of claim 21 wherein said compound is N-(N',N'-dimethylaminoethyl)-1-methyl-4-{1-methyl-4-[4-(4,4-bis-(2-chloroethyl)aminobenzylamino)-1-methylimidazole-2-carboxamido]imidazole-2-carboxamido}imidazole-2-carboxamide.

35. The method of claim 21 wherein said compound is N-(N',N'-dimethylaminoethyl)-1-methyl-4-{1-methyl-4-[4-(4,4-bis-(2-chloroethyl)aminobenzylamino)-1-methylimidazole-2-carboxamido]imidazole-2-carboxamido}imidazole-2-carboxamide.

36. The method of claim 21 wherein said compound is N-(N',N'-dimethylaminoethyl)-1-methyl-4-{4-[4,4-bis(2-chloroethyl)aminophenyl-1-butanamido]-1-methylimidazole-2-carboxamido}imidazole-2-carboxamide.

37. The method of claim 21 wherein said compound is N-(N',N'-dimethylaminoethyl)-1-methyl-4-{1-methyl-4-[4-(4,4-bis(2-chloroethyl)aminophenyl-1-butanamido)-1-methylimidazole-2-carboxamido]imidazole-2-carboxamido}imidazole-2-carboxamide.

38. The method of claim 21 wherein said compound is N-(N',N'-dimethylaminoethyl)-1-methyl-4-[4-(chloroacetamido)-1-methylimidazole-2-carboxamido]imidazole-2-carboxamide.

39. The method of claim 21 wherein said compound N-(N',N'-dimethylaminoethyl)-1-methyl-4-[4-(bromoacetamido)-1-methylimidazole-2-carboxamido]imidazole-2-carboxamide.

40. The method of claim 21 wherein said therapeutically effective amount is from about 0.01 to about 100 mg/kg body weight.

41. A pharmaceutical composition comprising a compound which has the formula:

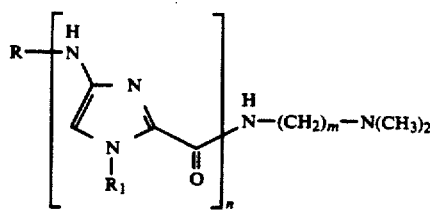

wherein
m is 0 to 4;
n is 2 to 4;
each $R_1$ is the same or different and is hydrogen or $C_1-C_4$ alkyl; and R is a DNA alkylating moiety.

42. The composition of claim 41 wherein said DNA alkylating moiety is a nitrogen mustard, nitrosourea, aziridine, methanesulfonate ester or epoxide.

43. The composition of claim 41 wherein R is
—$CO(CH_2)_p R_3$;
—$CO(CH_2)_p CH(R_3)_2$;
—$CO(CH_2)_p C(R_3)_3$;
—$(CH_2)_p AN(R_4)_2$; or
—$(CO)(CH_2)_p AN(R_4)_2$,
wherein p is 0–4; $R_3$ is halogen; A is a divalent ortho-, meta- or para-substituted phenyl group; and $R_4$ is $C_2-C_4$ alkyl 2-substituted by halogen, or a pharmaceutically acceptable salt thereof and a pharmaceutically acceptable carrier.

44. The composition of claim 41 wherein said compound is present in an amount to provide an effective dose of about 0.1 mg to about 100 mg/kg body weight.

* * * * *

UNITED STATES PATENT AND TRADEMARK OFFICE
CERTIFICATE OF CORRECTION

PATENT NO. : 5,273,991

DATED : December 28, 1993

INVENTOR(S) : Moses N. F. Lee

It is certified that error appears in the above-indentified patent and that said Letters Patent is hereby corrected as shown below:

On the Title Page, ITEM: [54], and Column 1, lines 1-3: "IMIDAZOLE-CONTAINING COMPOSITIONS AND METHODS OF USE THEREOF ANALOGS OF DISTAMYCIN" should read --IMIDAZOLE-CONTAINING ANALOGS OF DISTAMYCIN, COMPOSITIONS AND METHODS OF USE THEREOF--

On the Title Page, Item: [21]: "21,888" should read --921,888--

Column 2, line 19: "netrosin" should read --netropsin--

Column 2, line 25: "Less" should read --Lee--

Column 2, line 30: "decadeosyribonucleotide" should read --decadeoxyribonucleotide--

Column 2, line 36: "discloses" should read --disclose--

Column 2, line 37: "netrosin" should read --netropsin--

Column 5, line 12: after "methods" insert --.--

Column 6, line 4: "($CH_3CH$)" should read --($CH_3CN$)--

Column 7, line 51: after "others" insert --.--

UNITED STATES PATENT AND TRADEMARK OFFICE
CERTIFICATE OF CORRECTION

PATENT NO. : 5,273,991
DATED : December 28, 1993
INVENTOR(S) : Moses N. F. Lee

It is certified that error appears in the above-indentified patent and that said Letters Patent is hereby corrected as shown below:

```
Column 7, line 52:   after "solvents" insert --.--
Column 15, line 38:  before "s" insert --(--
Column 15, line 41:  "5.2" should read --45.2--
Column 16, line 11:  after "powder" insert --.--
Column 17, line 21:  before "0.0781" insert --(--
Column 18, line 6:   before "relative" insert --(--
Column 20, line 29:  after "spectrum" insert --.--
Column 20, line 35:  "(dA dT)" should read --(dA.dT)--
Column 20, line 35:  "(dG dC)" should read --(dG.dC)--
Column 21, line 53:  "(dG dC)" should read --(dG.dC)--
```

UNITED STATES PATENT AND TRADEMARK OFFICE
CERTIFICATE OF CORRECTION

PATENT NO. : 5,273,991

DATED : December 28, 1993

INVENTOR(S) : Moses N. F. Lee

It is certified that error appears in the above-indentified patent and that said Letters Patent is hereby corrected as shown below:

Column 25, line 19, Claim 2: after "is" insert --a--

Signed and Sealed this

Fourteenth Day of March, 1995

BRUCE LEHMAN

*Attest:*

*Attesting Officer*  *Commissioner of Patents and Trademarks*